(12) United States Patent
McGowan et al.

(10) Patent No.: US 11,622,779 B2
(45) Date of Patent: Apr. 11, 2023

(54) PHOTOACOUSTIC PRESSURE WAVE GENERATION FOR INTRAVASCULAR CALCIFICATION DISRUPTION

(71) Applicant: Boston Scientific Scimed, Inc., Maple Grove, MN (US)

(72) Inventors: Roger W. McGowan, Otsego, MN (US); Binh C. Tran, Minneapolis, MN (US); Christopher Smuk, Champlin, MN (US); Daniel Frank Massimini, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 836 days.

(21) Appl. No.: 16/654,561

(22) Filed: Oct. 16, 2019

(65) Prior Publication Data
US 2020/0129195 A1 Apr. 30, 2020

Related U.S. Application Data

(60) Provisional application No. 62/749,958, filed on Oct. 24, 2018.

(51) Int. Cl.
*A61B 17/22* (2006.01)
*A61B 18/24* (2006.01)
(Continued)

(52) U.S. Cl.
CPC ........ *A61B 17/2202* (2013.01); *A61B 18/245* (2013.01); *A61B 2017/22051* (2013.01);
(Continued)

(58) Field of Classification Search
CPC ........... A61B 2017/22085; A61B 2018/00404; A61B 2018/00994; A61B 2018/2261;
(Continued)

(56) References Cited

U.S. PATENT DOCUMENTS

| 5,372,138 A | 12/1994 | Crowley |
| 5,540,679 A | 7/1996 | Fram |

(Continued)

FOREIGN PATENT DOCUMENTS

| CN | 102057422 | 5/2011 |
| CN | 109223100 | 1/2019 |

(Continued)

OTHER PUBLICATIONS

E Marín et al 1996 J. Phys. D: Appl. Phys. 29 981-986 (Year: 1996).*

(Continued)

*Primary Examiner* — Carl H Layno
*Assistant Examiner* — Joshua Andrew Schum-Houck
(74) *Attorney, Agent, or Firm* — Roeder & Broder LLP; James P. Broder

(57) ABSTRACT

A photoacoustic catheter can include an elongate shaft and a first photoacoustic transducer. The elongate shaft can extend from a proximal region to a distal region and can include a first light guide that is in optical communication with a light source. The first photoacoustic transducer can be disposed within the distal region of the elongate shaft and can be in optical communication with the first light guide. The first photoacoustic transducer can impart acoustic pressure waves upon a calcified lesion to induce fractures. The first photoacoustic transducer can include a light-absorbing material and a thermal expansion material that can be in contact with one another.

20 Claims, 10 Drawing Sheets

(51) Int. Cl.
  *A61B 18/00* (2006.01)
  *A61B 18/26* (2006.01)
  *A61B 18/22* (2006.01)

(52) U.S. Cl.
  CPC ............. *A61B 2017/22085* (2013.01); *A61B 2018/00404* (2013.01); *A61B 2018/00994* (2013.01); *A61B 2018/2261* (2013.01); *A61B 2018/266* (2013.01)

(58) Field of Classification Search
  CPC .... A61B 2018/266; A61B 2018/00285; A61B 2018/2211; A61B 2018/2272; A61B 2018/2294; A61B 2018/263; A61B 18/26
  See application file for complete search history.

(56) References Cited

U.S. PATENT DOCUMENTS

| | | | |
|---|---|---|---|
| 5,609,606 A | 3/1997 | O'Boyle | |
| 5,611,807 A | 3/1997 | O'Boyle | |
| 5,772,609 A | 6/1998 | Nguyen et al. | |
| 6,080,119 A | 6/2000 | Schwarze et al. | |
| 6,123,923 A | 9/2000 | Unger | |
| 6,139,510 A | 10/2000 | Palermo | |
| 6,186,963 B1 | 2/2001 | Schwarze et al. | |
| 6,210,404 B1 | 4/2001 | Shadduck | |
| 6,514,203 B2 | 2/2003 | Bukshpan | |
| 6,524,251 B2 | 2/2003 | Rabiner et al. | |
| 6,607,502 B1 | 8/2003 | Maguire et al. | |
| 6,652,547 B2 | 11/2003 | Rabiner et al. | |
| 6,849,994 B1 | 2/2005 | White et al. | |
| 7,470,240 B2 | 12/2008 | Schultheiss et al. | |
| 7,810,395 B2 | 10/2010 | Zhou | |
| 7,867,178 B2 | 1/2011 | Simnacher | |
| 7,985,189 B1 | 7/2011 | Ogden et al. | |
| 8,162,859 B2 | 4/2012 | Schultheiss et al. | |
| 8,166,825 B2 | 5/2012 | Zhou | |
| 8,556,813 B2 | 10/2013 | Cashman et al. | |
| 8,574,247 B2 | 11/2013 | Adams et al. | |
| 8,709,075 B2 | 4/2014 | Adams et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,044,619 B2 | 6/2015 | Hawkins et al. | |
| 9,072,534 B2 | 7/2015 | Adams et al. | |
| 9,131,949 B2 | 9/2015 | Coleman et al. | |
| 9,138,249 B2 | 9/2015 | Adams et al. | |
| 9,180,280 B2 | 11/2015 | Hawkins et al. | |
| 9,220,521 B2 | 12/2015 | Hawkins et al. | |
| 9,237,984 B2 | 1/2016 | Hawkins et al. | |
| 9,289,224 B2 | 3/2016 | Adams et al. | |
| 9,320,530 B2 | 4/2016 | Grace | |
| 9,333,000 B2 | 5/2016 | Hakala et al. | |
| 9,375,223 B2 | 6/2016 | Wallace | |
| 9,433,428 B2 | 9/2016 | Hakala et al. | |
| 9,510,887 B2 | 12/2016 | Burnett | |
| 9,554,815 B2 | 1/2017 | Adams | |
| 9,555,267 B2 | 1/2017 | Ein-gal | |
| 9,566,209 B2 | 2/2017 | Katragadda et al. | |
| 9,579,114 B2 | 2/2017 | Mantell et al. | |
| 9,642,673 B2 | 5/2017 | Adams et al. | |
| 9,730,715 B2 | 8/2017 | Adams | |
| 9,814,476 B2 | 11/2017 | Adams et al. | |
| 9,861,377 B2 | 1/2018 | Mantell | |
| 9,867,629 B2 | 1/2018 | Hawkins | |
| 9,955,946 B2 | 5/2018 | Miller et al. | |
| 9,993,292 B2 | 6/2018 | Adams et al. | |
| 10,039,561 B2 | 8/2018 | Adams et al. | |
| 10,159,505 B2 | 12/2018 | Hakala et al. | |
| 10,201,387 B2 | 2/2019 | Grace et al. | |
| 10,842,567 B2 | 11/2020 | Grace et al. | |
| 2001/0051784 A1 | 12/2001 | Brisken | |
| 2003/0176873 A1 | 9/2003 | Chernenko et al. | |
| 2004/0002677 A1 | 1/2004 | Gentsler | |
| 2004/0073251 A1 | 4/2004 | Weber | |
| 2004/0097996 A1 | 5/2004 | Rabiner | |
| 2004/0162508 A1 | 8/2004 | Uebelacker | |
| 2004/0249401 A1 | 12/2004 | Rabiner | |
| 2005/0113722 A1 | 5/2005 | Schultheiss | |
| 2005/0171527 A1 | 8/2005 | Bhola | |
| 2006/0190022 A1 | 8/2006 | Beyar et al. | |
| 2006/0241524 A1 | 10/2006 | Lee et al. | |
| 2007/0060990 A1 | 3/2007 | Satake | |
| 2007/0088380 A1 | 4/2007 | Hirszowicz et al. | |
| 2007/0118057 A1 | 5/2007 | Ein-Gal | |
| 2007/0255270 A1 | 11/2007 | Carney | |
| 2007/0270897 A1 | 11/2007 | Skerven | |
| 2008/0097251 A1 | 4/2008 | Babaev | |
| 2008/0108867 A1* | 5/2008 | Zhou | A61B 8/12 606/7 |
| 2008/0132810 A1 | 6/2008 | Scoseria et al. | |
| 2008/0229837 A1 | 9/2008 | Zhou | |
| 2008/0296152 A1 | 12/2008 | Voss | |
| 2008/0319356 A1 | 12/2008 | Cain et al. | |
| 2009/0036803 A1 | 2/2009 | Warlick et al. | |
| 2009/0043300 A1 | 2/2009 | Reitmajer et al. | |
| 2009/0247945 A1 | 10/2009 | Levit | |
| 2010/0016862 A1 | 1/2010 | Hawkins et al. | |
| 2010/0036294 A1 | 2/2010 | Mantell et al. | |
| 2010/0114020 A1 | 5/2010 | Hawkins et al. | |
| 2010/0114065 A1 | 5/2010 | Hawkins | |
| 2010/0198114 A1 | 8/2010 | Novak et al. | |
| 2010/0199773 A1 | 8/2010 | Zhou | |
| 2010/0222786 A1 | 9/2010 | Kassab | |
| 2010/0256535 A1 | 10/2010 | Novak et al. | |
| 2011/0144502 A1 | 6/2011 | Zhou et al. | |
| 2011/0208185 A1 | 8/2011 | Diamant et al. | |
| 2011/0245740 A1 | 10/2011 | Novak et al. | |
| 2012/0071889 A1 | 3/2012 | Mantell et al. | |
| 2012/0095335 A1 | 4/2012 | Sverdlik et al. | |
| 2012/0116289 A1 | 5/2012 | Hawkins et al. | |
| 2012/0157892 A1 | 6/2012 | Reitmajer et al. | |
| 2012/0203255 A1 | 8/2012 | Hawkins et al. | |
| 2012/0221013 A1 | 8/2012 | Hawkins et al. | |
| 2013/0030431 A1 | 1/2013 | Adams | |
| 2013/0030447 A1 | 1/2013 | Adams | |
| 2013/0046207 A1 | 2/2013 | Capelli | |
| 2013/0197614 A1 | 8/2013 | Gustus | |
| 2013/0218054 A1 | 8/2013 | Sverdlik et al. | |
| 2013/0253466 A1 | 9/2013 | Campbell | |
| 2013/0345617 A1 | 12/2013 | Wallace | |
| 2014/0005576 A1 | 1/2014 | Adams | |
| 2014/0039513 A1 | 2/2014 | Hakala | |
| 2014/0052146 A1 | 2/2014 | Curtis et al. | |
| 2014/0052147 A1 | 2/2014 | Hakala et al. | |
| 2014/0058294 A1 | 2/2014 | Gross et al. | |
| 2014/0074111 A1 | 3/2014 | Hakala | |
| 2014/0180069 A1* | 6/2014 | Millett | A61B 8/12 600/463 |
| 2014/0180126 A1 | 6/2014 | Millett | |
| 2014/0180134 A1 | 6/2014 | Hoseit | |
| 2014/0257144 A1 | 9/2014 | Capelli et al. | |
| 2014/0257148 A1 | 9/2014 | Jie | |
| 2014/0276573 A1 | 9/2014 | Miesel | |
| 2014/0288570 A1 | 9/2014 | Adams | |
| 2015/0039002 A1 | 2/2015 | Hawkins | |
| 2015/0359432 A1 | 12/2015 | Ehrenreich | |
| 2016/0008016 A1 | 1/2016 | Cioanta et al. | |
| 2016/0095610 A1 | 4/2016 | Lipowski et al. | |
| 2016/0135828 A1 | 5/2016 | Hawkins et al. | |
| 2016/0183957 A1 | 6/2016 | Hakala et al. | |
| 2016/0184570 A1 | 6/2016 | Grace et al. | |
| 2016/0270806 A1 | 9/2016 | Wallace | |
| 2016/0234534 A1 | 11/2016 | Hawkins et al. | |
| 2016/0331389 A1 | 11/2016 | Hakala et al. | |
| 2016/0367274 A1 | 12/2016 | Wallace | |
| 2016/0367275 A1 | 12/2016 | Wallace | |
| 2017/0049463 A1 | 2/2017 | Popovic et al. | |

(56) References Cited

U.S. PATENT DOCUMENTS

| | | |
|---|---|---|
| 2017/0056035 A1 | 3/2017 | Adams |
| 2017/0119470 A1 | 5/2017 | Diamant et al. |
| 2017/0135709 A1 | 5/2017 | Nguyen et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0098779 A1 | 4/2018 | Betelia et al. |
| 2018/0153568 A1 | 6/2018 | Kat-kuoy |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0360482 A1 | 12/2018 | Nguyen |

FOREIGN PATENT DOCUMENTS

| | | |
|---|---|---|
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| EP | 0558297 A2 | 9/1993 |
| EP | 1179993 | 2/2002 |
| EP | 1946712 A1 | 7/2008 |
| EP | 2157569 | 2/2010 |
| EP | 2879595 | 6/2015 |
| EP | 2944264 A1 | 11/2015 |
| EP | 3318204 | 5/2018 |
| GB | 1082397 | 9/1967 |
| KR | 20050098932 | 10/2005 |
| KR | 20080040111 | 5/2008 |
| WO | WO0067648 | 11/2000 |
| WO | WO2009121017 | 10/2009 |
| WO | WO2009149321 A1 | 12/2009 |
| WO | WO2012025833 | 3/2012 |
| WO | WO2013119662 | 8/2013 |
| WO | WO2016089683 A1 | 6/2016 |
| WO | WO2016109739 | 7/2016 |
| WO | WO2018083666 | 5/2018 |

OTHER PUBLICATIONS

Noimark, Sacha, et al., "Carbon-Nanotube-PDMS Composite Coatings on Optical Fibers for All-Optical Ultrasound Imaging." Advanced Functional Materials. 2016, 26, 8390-8396.

Chen, Sung-Liang, "Review of Laser-Generated Ultrasound Transmitters and Their Applications to All-Optical Ultrasound Transducers and Imaging" Appl. Sci. 2017, 7, 25.

Colchester, Richard J., et al. "Laser-Generated ultrasound with optica fibres using functionalised carbon nanotube composite coatings." Appl. Phys. Lett. 104, 173504 (2014).

Poduval, Radhika K., et al. "Optical fiber ultrasound transmitter with electrospun carbon nanotube-polymer composite." Appl. Phys. Lett. 110, 223701 (2017).

Mohammadzadeh, M., et al. "Photoacoustic shock wave emission and cavitation from structured optical fiber tips." Appl. Phys. Lett. 108, 024101 (2016). AIP Publishing LLC.

Tian, Jiajun, et al. "Distributed fiber-optic laser-ultrasound generation based on ghost-mode of tilted fiber Bragg gratings." Optical Society of America. 2013.

Kim, Jinwook, et al. "Optical Fiber Laser-Generated-Focused-Ultrasound Transducers for Intravascular Therapies." IEEE 2017.

Kang, Hyun Wook, et al. "Enhanced photocoagulation with catheter-based diffusing optical device." Journal of Biomedical Optics 17 (11), 118001 (2012).

International Search Report and Written Opinion dated Jan. 3, 2020, in PCT Application Serial No. PCT/US2019/056579.

International Search Report and Written Opinion dated Jun. 27, 2018, in PCT Application Serial No. PCT/US2018/027121.

International Search Report and Written Opinion dated Jul. 20, 2018, in PCT Application Serial No. PCT/US2018/027801.

International Search Report and Written Opinion dated Jul. 20, 2018, in PCT Application Serial No. PCT/US2018/027784.

Communication Pursuant to Article 94(3) EPC, for European Patent Application No. 18185152.8, dated Jan. 16, 2019.

European Search Report, for European Patent Application No. 18185152.8, dated Dec. 20, 2018.

\* cited by examiner

PHOTOACOUSTIC PRESSURE WAVE GENERATION FOR INTRAVASCULAR CALCIFICATION DISRUPTION

BACKGROUND

Calcification within vessels in the body can be associated with an increased risk for major adverse events, such as myocardial infarction, embolism, deep vein thrombosis, stroke, and the like. Severely calcified vascular lesions can be difficult to treat and achieve patency for a physician in a clinical setting.

Calcified vascular lesions may be treated using interventions such as drug therapy, balloon angioplasty, atherectomy, stent placement, vascular graft bypass, to name a few. Such interventions may not always be ideal or may require subsequent treatment to address the lesion.

SUMMARY

The present invention is directed toward a photoacoustic catheter for placement within a blood vessel having a vessel wall. The photoacoustic catheter can be used for treating a calcified lesion within or adjacent to the vessel wall. In various embodiments, the photoacoustic catheter includes an elongate shaft and a first photoacoustic transducer. The elongate shaft can extend from a proximal region to a distal region. The elongate shaft can include a first light guide that is in optical communication with a light source. In certain embodiments, the first photoacoustic transducer can be disposed within the distal region of the elongate shaft. The first photoacoustic transducer can be in optical communication with the first light guide. The first photoacoustic transducer can be adapted to impart acoustic pressure waves upon the calcified lesion to induce fractures in the calcified lesion. Further, in various embodiments, the first photoacoustic transducer can include a light-absorbing material and a thermal expansion material. In some such embodiments, the thermal expansion material is in thermal contact with the light absorbing material. In some embodiments, the thermal expansion material can be selected from a group consisting of polydimethylsiloxane (PDMS), polytetrafluoroethylene (PTFE), polyimide, polyisobutylene (PIB), PIB polyurethane, polyurethanes, styrene isoprene butadiene, ethylene propylene polyacrylic, ethylene acrylic, fluorosilicone, polybutadiene, polyisoprene, and thermoplastic elastomers.

In some embodiments, the light-absorbing material can be selected from the group consisting of nanoparticles, carbon nanotubes, candle soot, candle soot nanoparticles, carbon black, a nanotube array, multiwall carbon nanotubes, and light absorbing dye.

In certain applications, the first light guide can be an optical fiber and the light source can be a laser.

In various embodiments, the photoacoustic catheter can also include a second light guide within the elongate shaft, and a second photoacoustic transducer. The second light guide can be in optical communication with the light source. The second photoacoustic transducer can be disposed within the distal region of the elongate shaft. The second photoacoustic transducer can be in optical communication with the second light guide. The second photoacoustic transducer can be adapted to impart acoustic pressure waves upon the calcified lesion to induce fractures in the calcified lesion. Further, in some embodiments, the second photoacoustic transducer can include a light-absorbing material and a thermal expansion material.

In some embodiments, the distal end of the first light guide has a shape selected from the group consisting of a cylindrical end, an angled end, a tapered end, and a conical end.

In certain embodiments, the distal end of the first light guide has a side surface and a diverter. In some such embodiments, the diverter can direct light in the first light guide toward the side surface. The diverter can include one of a reflecting element and a refracting element.

In various embodiments, the distal end of the first light guide has a side surface, and the first photoacoustic transducer is positioned on the side surface of the first light guide.

In some embodiments, the photoacoustic catheter can also include a second photoacoustic transducer and a second fiber diffuser. In certain embodiments, each fiber diffuser can direct light from the first light guide to exit the first light guide at the side surface. The side surface can be in optical communication with each of the photoacoustic transducers.

In certain embodiments, the first light guide can include a non-emitting portion. In some embodiments, the photoacoustic transducers can be axially spaced apart from one another with the non-emitting portion being disposed between the photoacoustic transducers.

In various applications, the first fiber diffuser can be selected from the group consisting of a machined portion of the first light guide, a laser-machined portion of the first light guide, fiber Bragg gratings, a fused splicing forming at least one internal mirror, and a splicing of two or more diffuse regions.

In certain embodiments, the photoacoustic catheter can also include an inflatable balloon disposed about the photoacoustic transducer and coupled to the elongate shaft. The inflatable balloon can shift between a collapsed configuration suitable for advancing a portion of the photoacoustic catheter through a patient's vasculature and an expanded configuration suitable for anchoring the portion of the photoacoustic catheter in position near the calcified lesion.

The present invention is also directed toward a method comprising the step of inducing fractures upon a calcified lesion that is within or adjacent to a vessel wall by generating acoustic pressure waves with a photoacoustic catheter that includes (i) a light guide and (ii) a photoacoustic transducer disposed within a distal region of the light guide and in optical communication with the light guide. In certain embodiments, the photoacoustic transducer can include a light-absorbing material and a thermal expansion material.

In some embodiments, the thermal expansion material is in thermal contact with the light absorbing material. Further, in certain embodiments, the thermal expansion material is selected from a group consisting of polydimethylsiloxane (PDMS), polytetrafluoroethylene (PTFE), polyimide, polyisobutylene (PIB), PIB polyurethane, polyurethanes, styrene isoprene butadiene, ethylene propylene polyacrylic, ethylene acrylic, fluorosilicone, polybutadiene, polyisoprene, and thermoplastic elastomers.

In various embodiments, the light-absorbing material is selected from the group consisting of nanoparticles, carbon nanotubes, candle soot, candle soot nanoparticles, carbon black, a nanotube array, multiwall carbon nanotubes, and light absorbing dye.

In some embodiments, the light guide is an optical fiber and the light source is a laser.

In certain embodiments, The method also includes the step of diverting light in the light guide toward a side surface of the light guide with a diverter that includes one of a reflecting element and a refracting element.

In various embodiments, the method also includes the step of directing light from the light guide to exit the light guide at a side surface of the light guide with a fiber diffuser. In some such embodiments, the side surface can be in optical communication with the photoacoustic transducer.

The present invention is also directed toward a photoacoustic catheter for treating a calcified lesion. In various embodiments, the photoacoustic catheter can include an elongate shaft extending from a proximal region to a distal region. In certain embodiments, the elongate shaft can include a light guide that includes an optical fiber. The light guide can be in optical communication with a light source that includes a laser. The light guide can include a side surface and a diverter, with the diverter directing light in the light guide toward the side surface. The diverter can include one of a reflecting element and a refracting element. Further, the photoacoustic catheter can also include a photoacoustic transducer disposed within the distal region of the elongate shaft. The photoacoustic transducer can be in optical communication with the light guide, the first photoacoustic transducer can be adapted to selectively impart acoustic pressure waves upon the calcified lesion to induce fractures in the calcified lesion. The photoacoustic transducer can include a light-absorbing material and a thermal expansion material.

In various embodiments, the light-absorbing material can be selected from the group consisting of nanoparticles, carbon nanotubes, candle soot, candle soot nanoparticles, carbon black, a nanotube array, multiwall carbon nanotubes, and light absorbing dye.

Further, in certain embodiments, the thermal expansion material can be selected from the group consisting of polydimethylsiloxane (PDMS), polytetrafluoroethylene (PTFE), polyimide, polyisobutylene (PIB), PIB polyurethane, polyurethanes, styrene isoprene butadiene, ethylene propylene polyacrylic, ethylene acrylic, fluorosilicone, polybutadiene, polyisoprene, and thermoplastic elastomers.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1:
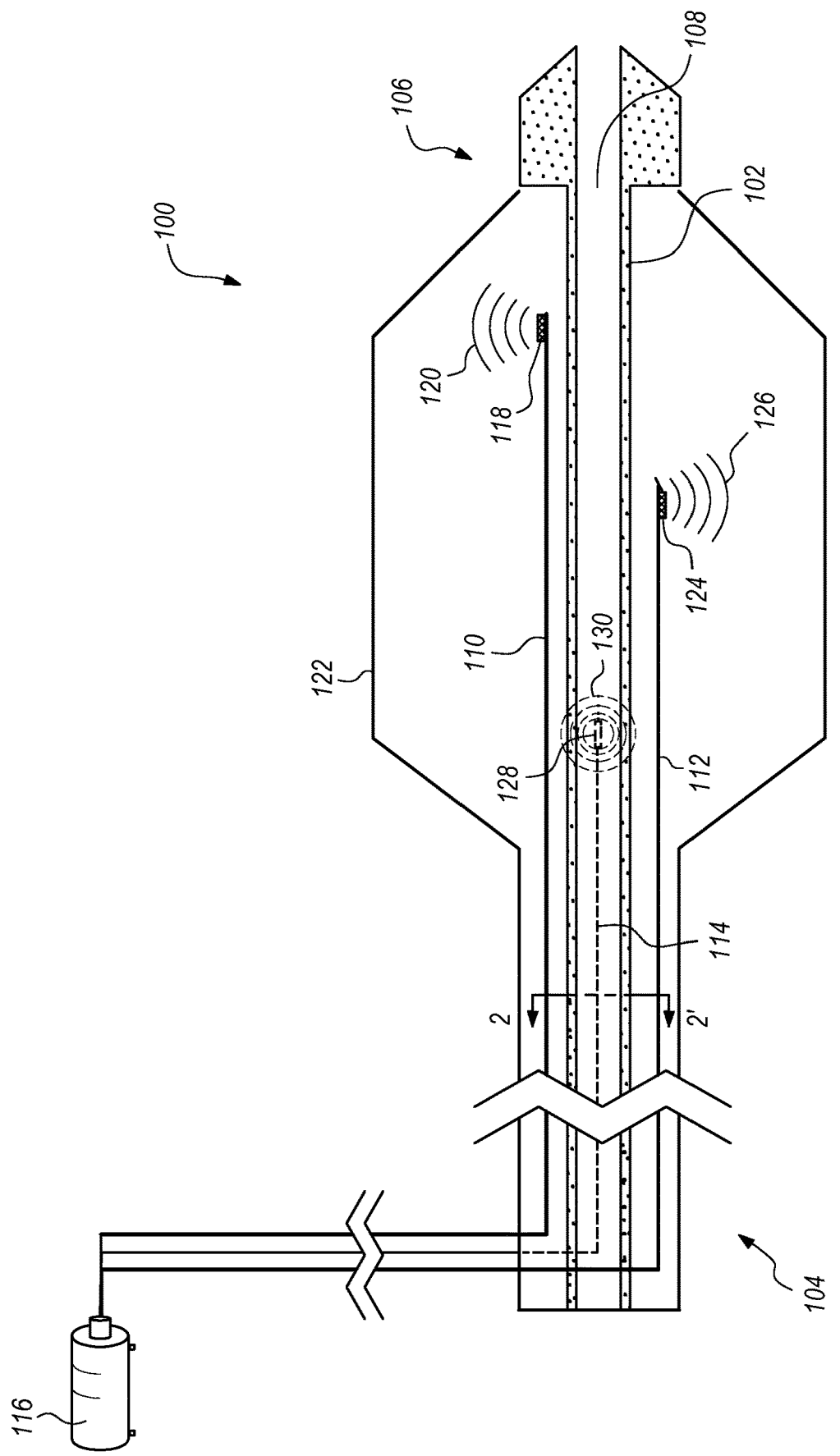
FIG. 1 is a simplified, schematic cross-sectional view of one embodiment of a photoacoustic catheter having features of the present invention.

While embodiments are susceptible to various modifications and alternative forms, specifics thereof have been shown by way of example and drawings, and are described in detail. It is understood, however, that the scope herein is not limited to the particular embodiments described. On the contrary, the intention is to cover modifications, equivalents, and alternatives falling within the spirit and scope herein.

DESCRIPTION

Treatment of calcified vascular lesions can reduce major adverse events or death in affected subjects. A major adverse event is one that can occur anywhere within the body due to the presence of a calcified vascular lesion. Major adverse events can include, but are not limited to major adverse cardiac events, major adverse events in the peripheral or central vasculature, major adverse events in the brain, major adverse events in the musculature, or major adverse events in any of the internal organs.

The systems and methods disclosed herein describe the use of pressure waves for intravascular calcification disruption. In various embodiments herein, the pressure wave generation is accomplished using a photoacoustic catheter adapted for placement within a blood vessel. The photoacoustic catheters are adapted to be in optical communication with a light source and are equipped with one or more photoacoustic transducers adapted to impart acoustic pressure waves upon a calcified lesion. Examples of such photoacoustic catheters can generate acoustic waves in the range of 1 to 30 megapascals, or 2 megapascals to 25 megapascals. A photoacoustic catheter can include an inflatable balloon or can be used in conjunction with a balloon catheter. It is also possible for a photoacoustic catheter to be used without an inflatable balloon structure, such as where the photoacoustic catheter is in the form of a guidewire.

As used herein, the term "photoacoustic" describes the property of a material emitting pressure waves in response to being illuminated by a light source.

As used herein, the terms "pressure wave", "acoustic wave" or "sound wave", can be used interchangeably, and describe propagating a pressure disturbance in gaseous, liquid, or solid material medium, including vibrational waves, sound waves, ultrasonic waves and acoustic shock waves.

As used herein, the terms "calcified lesion" or "calcified vascular lesion", can be used interchangeably, and describe any calcified region within or adjacent to a vessel wall.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

It is appreciated that the photoacoustic catheters herein can include many different forms which can vary. Referring now to FIG. 1, a schematic cross-sectional view of a photoacoustic catheter 100 (also sometimes referred to herein simply as a "catheter") is shown in accordance with various embodiments herein. The photoacoustic catheter 100 can be adapted for placement within a blood vessel having a vessel wall. The photoacoustic catheter 100 can be used to treat a calcified vascular lesion found within or adjacent to the vessel wall. The photoacoustic catheter 100 can include an elongate shaft 102 extending from a proximal region 104 to a distal region 106, and can also include a lumen 108. In some embodiments, the photoacoustic catheter 100 can have a distal end opening and can accommodate and be tracked over a guide wire to a treatment location. In some embodiments, the photoacoustic catheter 100 does not include the lumen 108. The photoacoustic catheter 100 can include an inflatable balloon 122. In some embodiments, the photoacoustic catheter 100 does not include the inflatable balloon 122. In embodiments where the elongate shaft 102 does not include a lumen 108 to be accessed by a caregiver, the elongate shaft 102 can be configured to allow the catheter 100 to be steered through a patient's vasculature.

The elongate shaft 102 of photoacoustic catheter 100 can include a first light guide 110 that is in optical communication with a light source 116. In some embodiments, the first light guide 110 can include an optical fiber and the light source 116 can include a laser. The light source 116 can be in optical communication with the first light guide 110 at least at a proximal region 104 of the elongate shaft 102. The photoacoustic catheter 100 can further include a first photoacoustic transducer 118 disposed within the distal region 106 of the elongate shaft 102. The first photoacoustic transducer 118 can be in optical communication with the first light guide 110. The first photoacoustic transducer 118 can be adapted to impart acoustic pressure waves upon a calcified lesion to induce fractures in the calcified lesion. A schematic depiction of an exemplary acoustic pressure wave 120 as generated by the first photoacoustic transducer 118 is shown. The first photoacoustic transducer 118 can be formed from a light-absorbing material and a thermal expansion material, both of which are discussed in more detail herein.

It is appreciated that, photoacoustic catheter 100 can include more than one light guide. In some embodiments, photoacoustic catheter 100 can include a second light guide 112. The second light guide can be in optical communication with the light source 116 at a proximal region 104 of the elongate shaft 102. The second light guide 112 can include a second photoacoustic transducer 124 disposed within the distal region 106 of the elongate shaft 102. The second photoacoustic transducer 124 can be in optical communication with the second light guide 112. The second photoacoustic transducer 124 can be adapted to impart acoustic pressure waves upon a calcified lesion to induce fractures in the calcified lesion. A schematic depiction of an exemplary acoustic pressure wave 126 as generated by the second photoacoustic transducer 126 is shown. In some embodiments, the first photoacoustic transducer and second photoacoustic transducer can be configured to be radially offset from each other by about 45 degrees or more. In some embodiments, a plurality of light guides are evenly spaced and radially offset from each other so that where there are n light guides, they are spaced apart by 360 degrees divided by n. The second photoacoustic transducer 124 can be formed from a light-absorbing material and a thermal expansion material, both of which are discussed in more detail herein.

The photoacoustic catheter 100 embodied in FIG. 1 further includes a third light guide 114 having a third photoacoustic transducer 128. The third photoacoustic transducer 128 can be adapted to impart acoustic pressure waves upon a calcified lesion to induce fractures in the calcified lesion. A schematic depiction of a third acoustic pressure wave 130 as generated by the third photoacoustic transducer 128 is shown. It is appreciated that the third photoacoustic transducer 128 can be formed from a light-absorbing material and a thermal expansion material, both of which are discussed in more detail herein. It is understood that the third light guide 114, the third photoacoustic transducer 128, and the third acoustic pressure wave 130, shown as dashed lines in FIG. 1, are on the opposite side of the photoacoustic catheter 100 from the viewer.

It is appreciated that the photoacoustic catheters herein can include any number of light guides. For example, in some embodiments, the photoacoustic catheters herein can include from one light guide to five light guides. In other embodiments, the photoacoustic catheters herein can include from five to fifteen light guides. In yet other embodiments, the photoacoustic catheters herein can include from ten light guides to thirty light guides. The photoacoustic catheters herein can include one, two, three, four, five, six, seven, eight, nine, ten, 11, 12, 13, 14, 15, 16, 17, 18, 19, 20, 21, 22, 23, 24, 25, 26, 27, 28, 29, or 30 light guides. It is appreciated that photoacoustic catheters herein can include any number of light guides that can fall within a range, wherein any of the forgoing numbers can serve as the lower or upper bound of the range, provided that the lower bound of the range is a value less than the upper bound of the range. In some embodiments, the photoacoustic catheters herein can include greater than 30 light guides. As used herein, any of the light guides (first, second, third, etc.) can be referred to simply as a "light guide".

Figure 2:
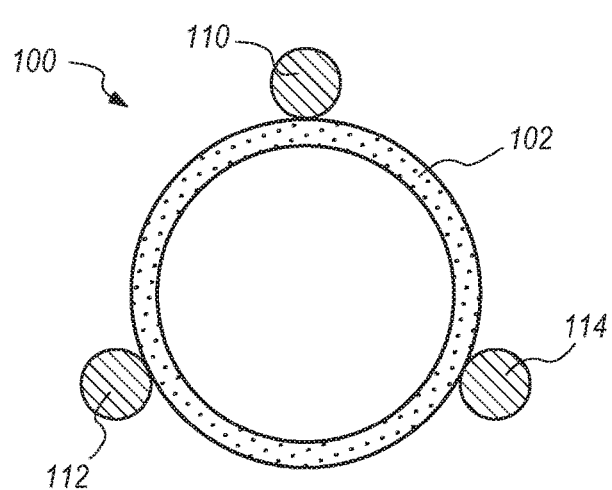
FIG. 2 is a schematic cross-sectional view of a portion of the photoacoustic catheter taken on line 2-2' in FIG. 1.
Figure 3:
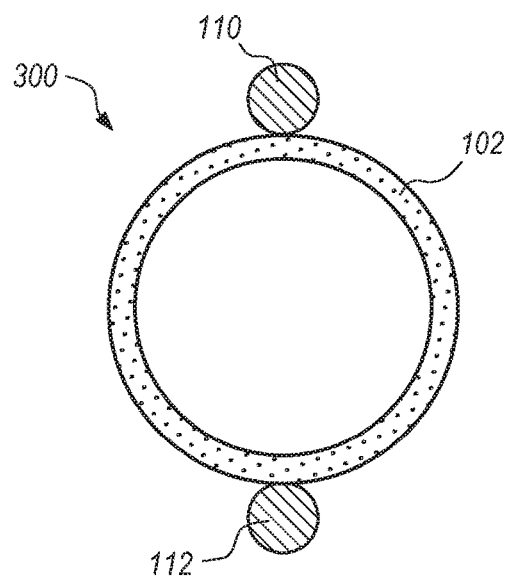
FIG. 3 is a schematic cross-sectional view of another embodiment of a portion of the photoacoustic catheter.
Figure 4:
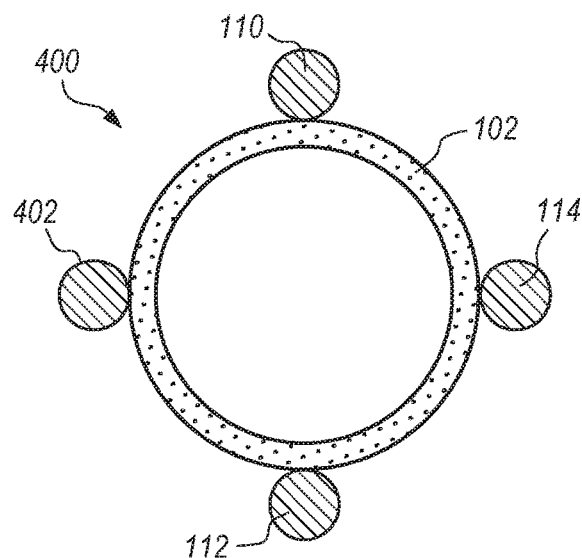
FIG. 4 is a schematic cross-sectional view of yet another embodiment of a portion of the photoacoustic catheter.
Figure 5:
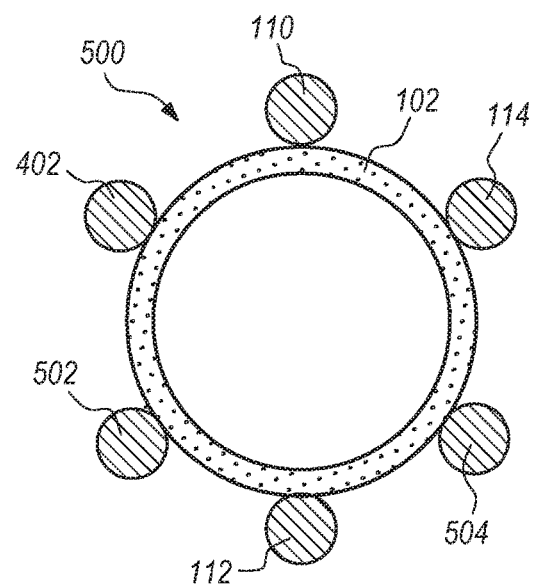
FIG. 5 is a schematic cross-sectional view of still another embodiment of a portion of the photoacoustic catheter.

Examples of photoacoustic catheters having multiple light guides at different positions around or near the circumference of the photoacoustic catheter are shown in FIGS. 2-5. Referring now to FIG. 2, a schematic cross-sectional view of the photoacoustic catheter 100 of FIG. 1 along line 2-2' in FIG. 1 is shown in accordance with various embodiments herein. Photoacoustic catheter 100 includes an elongate shaft 102, a first light guide 110, a second light guide 112, and a third light guide 114 separated by about 120 degrees around the circumference. Referring now to FIGS. 3-5 schematic cross-sectional views of additional configurations for photoacoustic catheters having multiple light guides are shown in accordance with various embodiments herein. The configuration of photoacoustic catheter 300 in FIG. 3 includes an elongate shaft 102, a first light guide 110 and a second light guide 112 separated by about 180 degrees around the circumference. The configuration of photoacoustic catheter 400 in FIG. 4 includes an elongate shaft 102, a first light guide 110, a second light guide 112, a third light guide 114, and a fourth light guide 402 separated by about 90 degrees around the circumference. The configuration of photoacoustic catheter 500 shown in FIG. 5 includes an elongate shaft 102, a first light guide 110, a second light guide 112, a third light guide 114, a fourth light guide 402, a fifth light guide 502, and a sixth light guide 504 separated by about 60 degrees around the circumference.

The light guides herein can assume many configurations about the elongate shaft of the photoacoustic catheters described herein. In some embodiments, the light guides can run parallel to the longitudinal axis of the elongate shaft of the photoacoustic catheter. When multiple light guides are present, the light guides can be radially offset from one another by about at least about or about 45 degrees. In some embodiments, the light guides can be radially offset from one another by at least about or about 60 degrees. In some embodiments, the light guides can be radially offset from one another by about at least about or 90 degrees. In some embodiments, the light guides can be radially offset from one another by at most about or about 180 degrees. In some embodiments, a plurality of light guides are evenly spaced and radially offset from each other so that where there are n light guides, they are spaced apart by 360 degrees divided by n. In some embodiments, each of the light guide locations shown in FIGS. 2-5 or otherwise described herein include two parallel light guides that are touching.

In other embodiments, the light guides can form a spiral configuration about the longitudinal axis of the elongate shaft of the photoacoustic catheter. In some embodiments, the spiral configuration can run clockwise about the longitudinal axis of the elongate shaft of the photoacoustic catheter, while in other embodiments the spiral configuration can run counter-clockwise about the longitudinal axis of the elongate shaft of the photoacoustic catheter. In some embodiments, the light guides can form a single helix, a double helix, a triple helix, or a quadruple helix about the longitudinal axis of the elongate shaft of the photoacoustic catheter.

Figure 6:
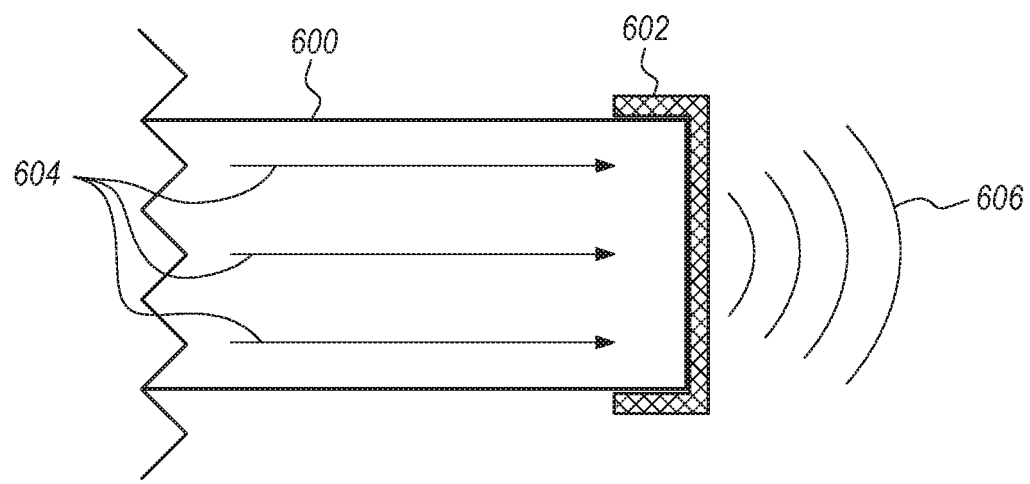
FIG. 6 is a schematic cross-sectional view of a portion of the photoacoustic catheter including one embodiment of a distal portion of a light guide.
Figure 7:
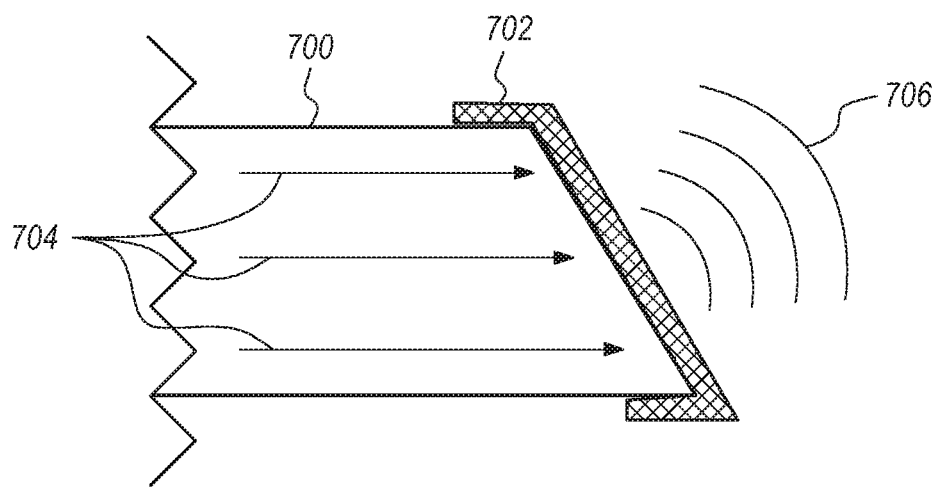
FIG. 7 is a schematic cross-sectional view of a portion of the photoacoustic catheter including another embodiment of the distal portion of the light guide.
Figure 8:
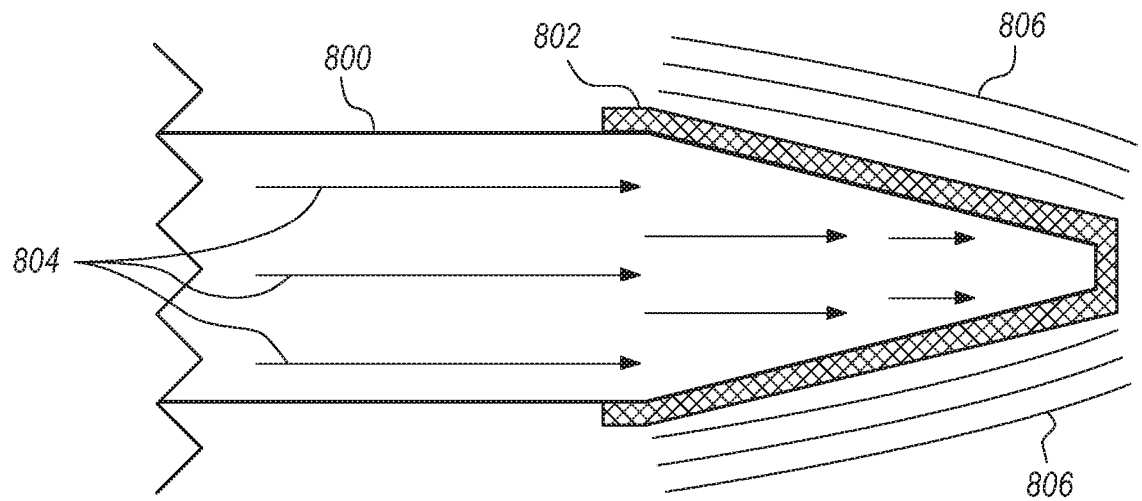
FIG. 8 is a schematic cross-sectional view of a portion of the photoacoustic catheter including another embodiment of the distal portion of the light guide.

The light guides herein can include one or more photoacoustic transducers, where each photoacoustic transducer can be in optical communication with the light guide within which it is disposed. In some embodiments, the photoacoustic transducers can be in optical communication with a distal end of the light guide. Referring now to FIGS. 6-9, schematic cross-sectional views of the distal ends of various shaped light guides are shown in accordance with various embodiments herein. In FIG. 6, a schematic cross-sectional view of a light guide 600 is shown. Light guide 600 includes a cylindrical end shape and a cylindrical-shaped photoacoustic transducer 602. Photoacoustic transducer 602 conforms to the cylindrical end of the light guide 600, and includes a circular end face and a sidewall, where the cylindrical sidewall is at an approximately 90 degree angle to the edge of the circular end face. Light guide 600 is configured such that light 604 travels from a light source (not shown) in the direction from the proximal region of the light guide to the distal region of the light guide 600, as indicated by the arrows. Light 604 within light guide 600 is directed to photoacoustic transducer 602, which converts light energy into an acoustic wave 606 at the distal region of the light guide 600.

In some embodiments, the end of the light guide can have an angled shape. By way of example, in FIG. 7 a schematic cross-sectional view of a light guide 700 is shown. Light guide 700 includes an angled end shape and an angle-shaped photoacoustic transducer 702. Photoacoustic transducer 702 conforms to the angled end shape of the light guide 700. Photoacoustic transducer 702 includes an angled end face and a cylindrical side wall extending from the edge of the angled end face. Light guide 700 is configured such that light 704 travels from a light source (not shown) in the direction from the proximal region of the light guide to the distal region of the light guide 700, as indicated by the arrows. Light 704 within light guide 700 is directed to photoacoustic transducer 702, which converts light energy into an acoustic wave 706 at the distal region of the light guide 700. It is appreciated that the direction of the acoustic wave 706 can be tailored by changing the angle of the end of the light guide 700.

In some embodiments, the end of the light guide can have a tapered shape. By way of example, in FIG. 8 a schematic cross-sectional view of a light guide 800 is shown. Light guide 800 includes a tapered end shape and a tapered photoacoustic transducer 802. Photoacoustic transducer 802 conforms to the tapered end shape of the light guide 800. Photoacoustic transducer 802 includes a circular end face and an angled sidewall converging at one end to the circular end face. At the opposite end of the angled sidewall, the photoacoustic transducer 802 includes a cylindrical sidewall that is parallel with the side surface of the light guide. Light guide 800 is configured such that light 804 travels from a light source (not shown) in the direction from the proximal region of the light guide to the distal region of the light guide, as indicated by the arrows. Light 804 within light guide 800 is directed to photoacoustic transducer 802, which converts light energy into an acoustic wave 806 at the distal region of the light guide 800. It is appreciated that in the case of light guide 800, the conical shape of the end can create an acoustic wave 806 that can extend radially about the end of the light guide 800.

In some embodiments, a diverter can be included with the light guide to direct light toward a side surface of the distal end of the light guide. A diverter can include any feature of the system herein that diverts light from the light guide away from its axial path toward a side surface of the light guide. Examples include a reflector, a refracting structure, and a fiber diffuser. These examples are discussed below in reference to FIGS. 9-13.

Figure 9:
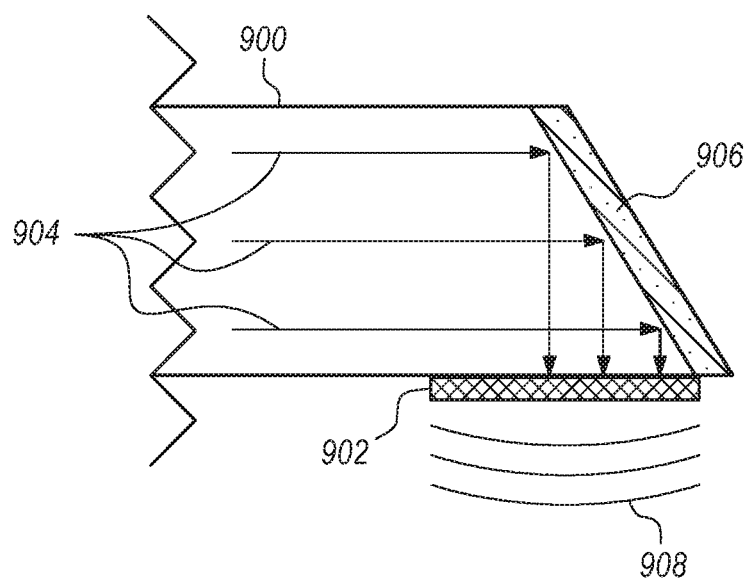
FIG. 9 is a schematic cross-sectional view of a portion of the photoacoustic catheter including yet another embodiment of the distal portion of the light guide.

Referring now to FIG. 9, a schematic cross-sectional view of a light guide 900 is shown. Light guide 900 includes an angled shape end having photoacoustic transducer 902 disposed on a side surface of its distal end. A side surface is a portion of the sidewall of the light guide. The light guide 900 also includes a diverter 906 at the distal end to direct the light within the light guide toward the side surface of the light guide at the site of the photoacoustic transducer 902. Light guide 900 is configured such that light 904 travels from a distal region to a proximal region of the light guide 900, as indicated by the arrows. Upon contact with the diverter 906, the light 904 is diverted, or reflected, within the light guide 900 to a photoacoustic transducer 902 in optical communication with a side surface of the light guide 900. Photoacoustic transducer 902 converts light energy into an acoustic wave 908 at the side surface of the distal region of the light guide 900.

The diverter 906 of light guide 900 can be made from a reflecting element or a refracting element. The diverter 906 can be made from a glass, a polymer, a mirror, or a reflective metal coating. It is appreciated that the angle of internal reflection by the diverter 906 can be adjusted by changing the angle of the distal end of light guide 900. It is further appreciated that the side surface of the light guide interfaces with the photoacoustic transducer 902.

The photoacoustic transducers disposed at the distal end of the light guides herein can assume the same shape as the distal end of the light guide, and include, but are not limited to a conical shape, a convex shape, a concave shape, a bulbous shape, a square shape, a stepped shape, a half-circle shape, an ovoid shape, and the like. It is also appreciated that the light guides of FIGS. 6-9 can further include additional photoacoustic transducers disposed along one or more side surfaces of the length of the light guide, as discussed further below in reference to FIGS. 10-12.

The light guides herein can individually include any number of photoacoustic transducers. For example, in some embodiments, each light guide herein can include from one photoacoustic transducer to ten photoacoustic transducers. In other embodiments, each light guide herein can include from five photoacoustic transducers to twenty photoacoustic transducers. In yet other embodiments, each light guide herein can include from 10 photoacoustic transducers to 40 photoacoustic transducers. The light guides herein can include one, two, three, four, five, six, seven, eight, nine, or ten photoacoustic transducers. The light guides herein can include 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 photoacoustic transducers. It is appreciated that light guides herein can include any number of photoacoustic transducers that can fall within a range, wherein any of the forgoing numbers can serve as the lower or upper bound of the range, provided that the lower bound of the range is a value less than the upper bound of the range. In some embodiments, the light guides herein can include more than 40 photoacoustic transducers.

The photoacoustic transducers herein can be placed in many configurations along the longitudinal axis of the individual light guides described herein. In some embodiments, two or more photoacoustic transducers can be disposed opposite one another on the longitudinal axis of the individual light guide. In other embodiments, the photoacoustic transducers can be radially disposed about the elongate shaft of the light guide. In some examples, the photoacoustic transducers are minimally spaced apart, such as by about 1 degree, 2 degrees, or 5 degrees. In some examples, the photoacoustic transducers can be radially offset from one another by at least about or about 30 degrees. In some embodiments, the photoacoustic transducers can be radially offset from one another by at least about or about 45 degrees. In some embodiments, the photoacoustic transducers can be radially offset from one another by at least about or about 60 degrees. In some embodiments, the photoacoustic transducers can be radially offset from one another by at least about or about 90 degrees. In other embodiments, the photoacoustic transducers can be radially offset from one another by at most about or about 180 degrees. In various examples, the locations of the photoacoustic transducers can be in the same locations where the light guides are positioned in FIGS. 2-5.

Figure 10:
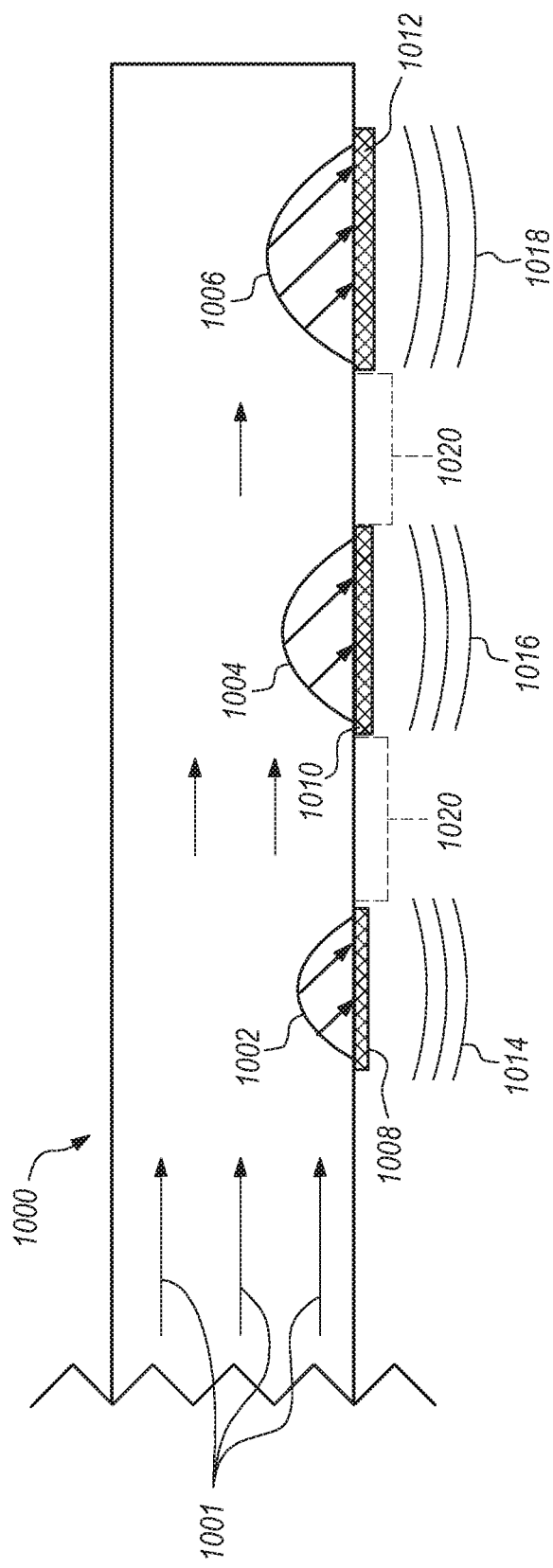
FIG. 10 is a schematic cross-sectional view of a portion of the photoacoustic catheter including still another embodiment of the distal portion of the light guide.

The light guides herein can include one or more fiber diffusers within the distal end to provide multiple selected regions within the light guide for the generation of acoustic waves. A fiber diffuser can be included as a part of the light guide that diverts light away from its axial path through the light guide and to a side surface. Referring now to FIG. 10, a schematic cross-sectional view of light guide 1000 is shown in accordance with various embodiments herein. Light guide 1000 includes a plurality of fiber diffusers including a first, second, and third fiber diffuser 1002, 1004, and 1006 positioned along the elongate shaft of the distal region of the light guide 1000. Each fiber diffuser directs light 1001 from the light guide 1000 to exit the light guide 1000 at a side surface thereof. The side surfaces of the light guide 1000 are in optical communication with one or more photoacoustic transducers and one or more fiber diffusers, such that the fiber diffusers and the photoacoustic transducers are in optical communication with one another.

By way of example, light guide 1000 includes a plurality of photoacoustic transducers including a first, second, and third photoacoustic transducer 1008, 1010, and 1012 positioned along the elongate shaft of the light guide 1000. The first, second, and third photoacoustic transducers 1008, 1010, and 1012 can be in optical communication with the first, second, and third fiber diffusers 1002, 1004, and 1006, respectively, at a plurality of side surfaces of light guide 1000. Light within each of the first, second, and third fiber diffusers 1002, 1004, and 1006 is directed to exit the light guide 1000 at a side surface and is absorbed by the first, second, and third photoacoustic transducers 1008, 1010, and 1012, respectively. Light energy can be absorbed by the photoacoustic transducers and converted into one or more acoustic waves, as indicated by acoustic waves 1014, 1016, and 1018. The photoacoustic transducers 1008, 1010, and 1012 of light guide 1000 can be axially spaced apart with at least one intervening non-emitting portion 1020 of the light guide 1000 disposed between the plurality of photoacoustic transducers.

In various examples, the photoacoustic transducers, fiber diffusers, or both vary in size along the length of the photoacoustic catheter. In various examples, the photoacoustic transducers, fiber diffusers or both increase in size moving toward the distal end. In the example of FIG. 10, the most proximal first fiber diffuser 1002 is smaller than the second fiber diffuser 1004, and the third fiber diffuser 1006 is larger than the second fiber diffuser 1004. In the example of FIG. 10, the most proximal photoacoustic transducer 1008 is smaller in surface area than the second photoacoustic transducer 1010, and the third photoacoustic transducer 1012 is larger in surface area than the second photoacoustic transducer 1010. As used herein, any of the fiber diffusers described herein, i.e. first, second, third, etc., can equally be referred to simply as a "fiber diffuser".

Figure 11:
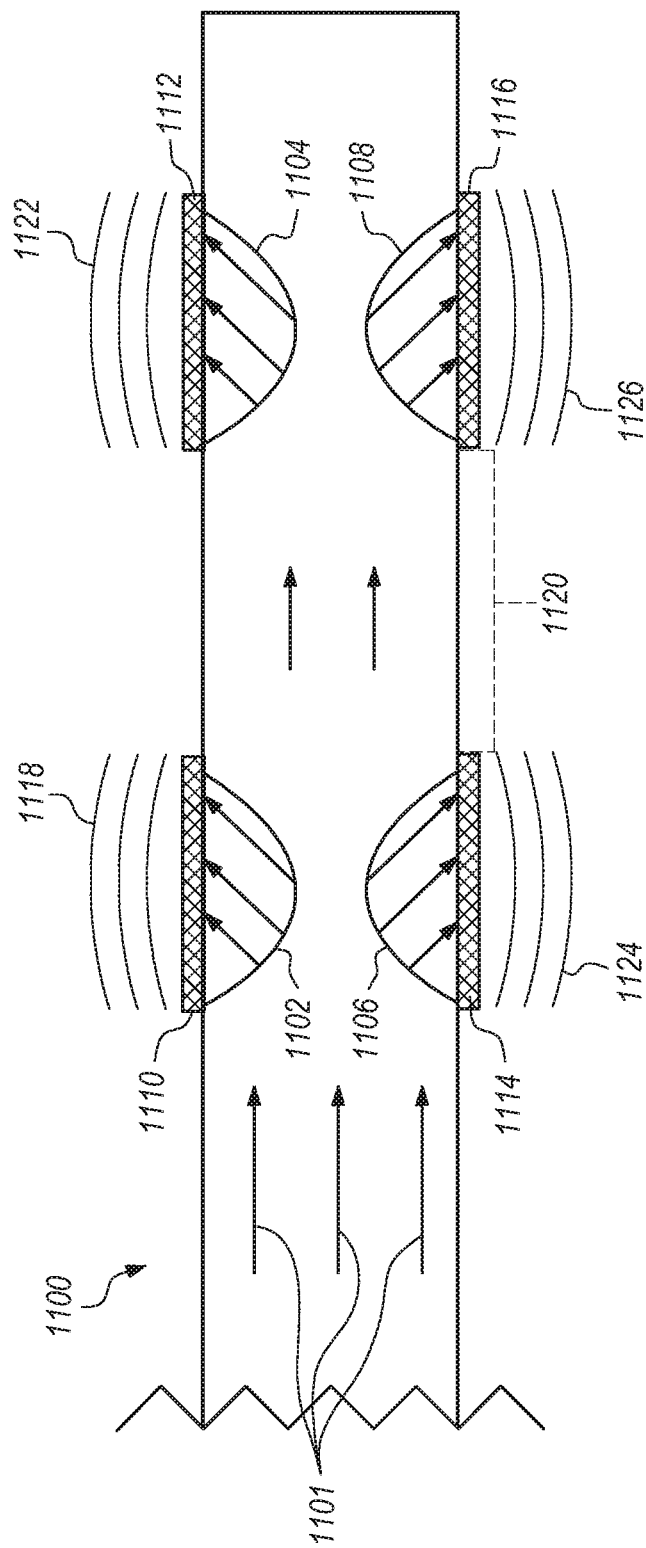
FIG. 11 is a schematic cross-sectional view of a portion of the photoacoustic catheter including but another embodiment of the distal portion of the light guide.

While the fiber diffusers and photoacoustic transducers of light guide 1000 are shown disposed on one side of light guide 1000, it is appreciated that the fiber diffusers and photoacoustic transducers can be disposed in many different positions. In various examples, fiber diffusers and photoacoustic transducers can be disposed opposite one another along the elongate shaft of the light guide. Referring now to FIG. 11, a schematic cross-sectional view of light guide 1100 is shown in accordance with various embodiments herein. Light guide 1100 includes fiber diffusers 1102, 1104, 1106, and 1108. Each fiber diffuser directs light 1101 from the light guide 1100 to exit the light guide 1100 at a side surface thereof. The side surfaces of the light guide 1100 are in optical communication with one or more photoacoustic transducers and one or more fiber diffusers, such that the fiber diffusers and the photoacoustic transducers are in optical communication with one another.

By way of example, light guide 1100 includes a plurality of photoacoustic transducers including a first, second, third, and fourth photoacoustic transducer 1110, 1112, 1114, and 1116, respectively, positioned along the elongate shaft of the light guide 1100. The first, second, third, and fourth photoacoustic transducers 1110, 1112, 1114, and 1116, respectively, can be in optical communication with the first, second, and third fiber diffusers 1102, 1104, 1106, and 1108, respectively, at a plurality of side surfaces of light guide 1100. Light within each of the first, second, and third fiber diffusers 1102, 1104, 1106, and 1108 is directed to exit the light guide 1100 at a side surface and is absorbed by the first, second, third, and fourth photoacoustic transducers 1110, 1112, 1114, and 1116, respectively. Light energy can be absorbed by the photoacoustic transducers and converted into one or more acoustic waves, as indicated by acoustic waves 1118, 1122, 1124, and 1126. The photoacoustic transducers 1110, 1112, 1114, and 1116 of light guide 1100 can be axially spaced apart with at least one intervening non-emitting portion 1120 of the light guide 1100 disposed between the plurality of photoacoustic transducers.

Figure 12:
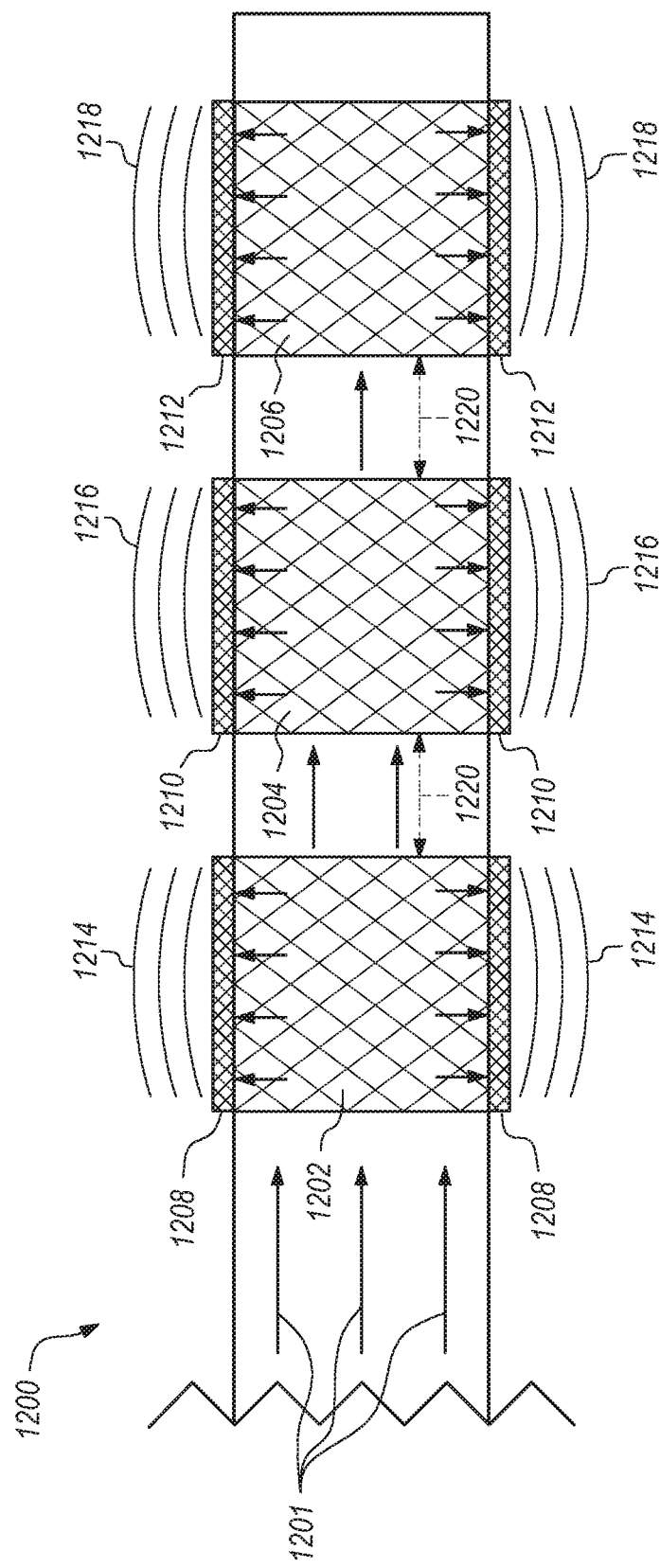
FIG. 12 is a schematic cross-sectional view of a portion of the photoacoustic catheter including another embodiment of the distal portion of the light guide.

In some embodiments, the fiber diffusers can be included within the light guide at one or more regions of the distal end. Referring now to FIG. 12 a schematic cross-sectional view of light guide 1200 is shown in accordance with various embodiments herein. Light guide 1200 includes a plurality of fiber diffusers including a first, second, and third fiber diffuser 1202, 1204, and 1206, respectively, positioned along the elongate shaft of the distal region of the light guide 1200. Each fiber diffuser directs light 1201 from the light guide 1200 to exit the light guide 1200 at a side surface thereof. The side surfaces of the light guide 1200 are in optical communication with one or more photoacoustic transducers, such that the fiber diffusers and the photoacoustic transducers are in optical communication with one another.

By way of example, light guide 1200 includes a plurality of photoacoustic transducers including a first, second, and third photoacoustic transducer 1208, 1210, and 1212, respectively, positioned along the elongate shaft of the light guide 1200. The first, second, and third photoacoustic transducers 1208, 1210, and 1212, respectively, can be in optical communication with the first, second, and third fiber diffusers 1202, 1204, and 1206, respectively, at a plurality of side surfaces of light guide 1200. Light 1201 within each of the first, second, and third fiber diffusers 1202, 1204, and 1206 is directed to exit the light guide 1200 at a side surface and is absorbed by the first, second, and third photoacoustic transducers 1208, 1210, and 1212, respectively. Light energy can be absorbed by the photoacoustic transducers and converted into one or more acoustic waves, as indicated by acoustic waves 1214, 1216, and 1218, each of which can be emitted as a radial wave about the light guide 1200. The photoacoustic transducers 1208, 1210, and 1212 of light guide 1200 can be axially spaced apart with at least one intervening non-emitting portion 1220 of the light guide 1200 disposed between the plurality of photoacoustic transducers. As used herein, any of the photoacoustic transducers referred to herein, i.e. first, second, third, etc., can equally be referred to simply as a "photoacoustic transducer".

The fiber diffusers and photoacoustic transducers shown in FIG. 12 include those having a cylindrical shape. By way of example, the fiber diffusers 1202, 1204, and 1206 are configured to span the entire circumference of light guide 1200, and as such, the fiber diffusers 1202, 1204, and 1206 are cylindrical fiber diffusers. The photoacoustic transducers 1208, 1210, and 1212 are configured to span the entire circumference of light guide 1200, and as such, photoacoustic transducers 1208, 1210, and 1212 are cylindrical transducers.

Figure 13:
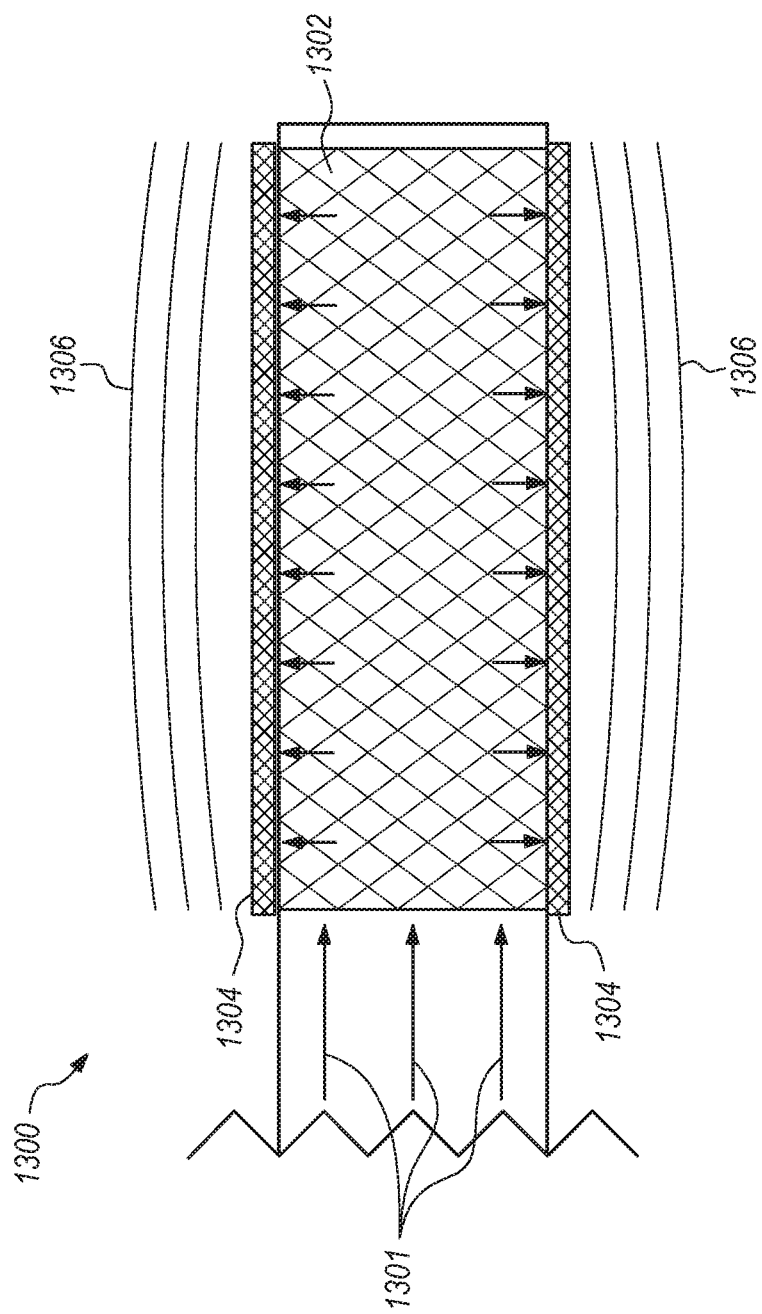
FIG. 13 is a schematic cross-sectional view of a portion of the photoacoustic catheter including still another embodiment of the distal portion of the light guide.

In some embodiments, a single large fiber diffuser can be included within the light guide at the distal end. Referring now to FIG. 13 a schematic cross-sectional view of light guide 1300 is shown in accordance with various embodiments herein. Light guide 1300 includes a single fiber diffuser 1302 positioned along the elongate shaft of the distal region of the light guide 1300. The fiber diffuser 1302 directs light 1301 to exit the light guide 1300 at a side surface thereof. The side surface of the light guide 1300 is in optical communication with photoacoustic transducer 1304 and fiber diffuser 1302, such that the fiber diffuser 1302 and the photoacoustic transducer 1304 are in optical communication with one another.

Light 1301 is absorbed by the photoacoustic transducer 1304 and converted into acoustic wave 1306 that can be emitted as a radial wave about the light guide 1300. The fiber diffuser 1302 and the photoacoustic transducer 1304 can be configured to span the entire circumference of light guide 1300. The fiber diffuser 1302 can be a cylindrical fiber diffuser. The photoacoustic transducer 1304 can be a cylindrical transducer. The side surface of the light guide disposed in between the fiber diffuser 1302 and the photoacoustic transducer 1304 can be a cylindrical side portion.

Figure 14:
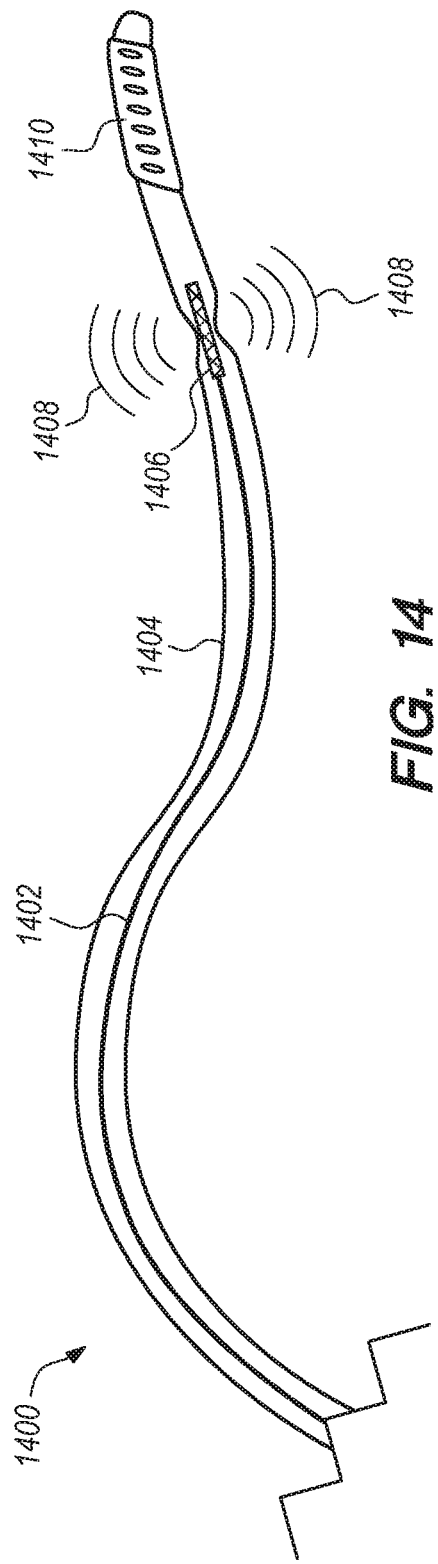
FIG. 14 is a schematic sectional view of an embodiment of a portion of the photoacoustic catheter.
Figure 15:
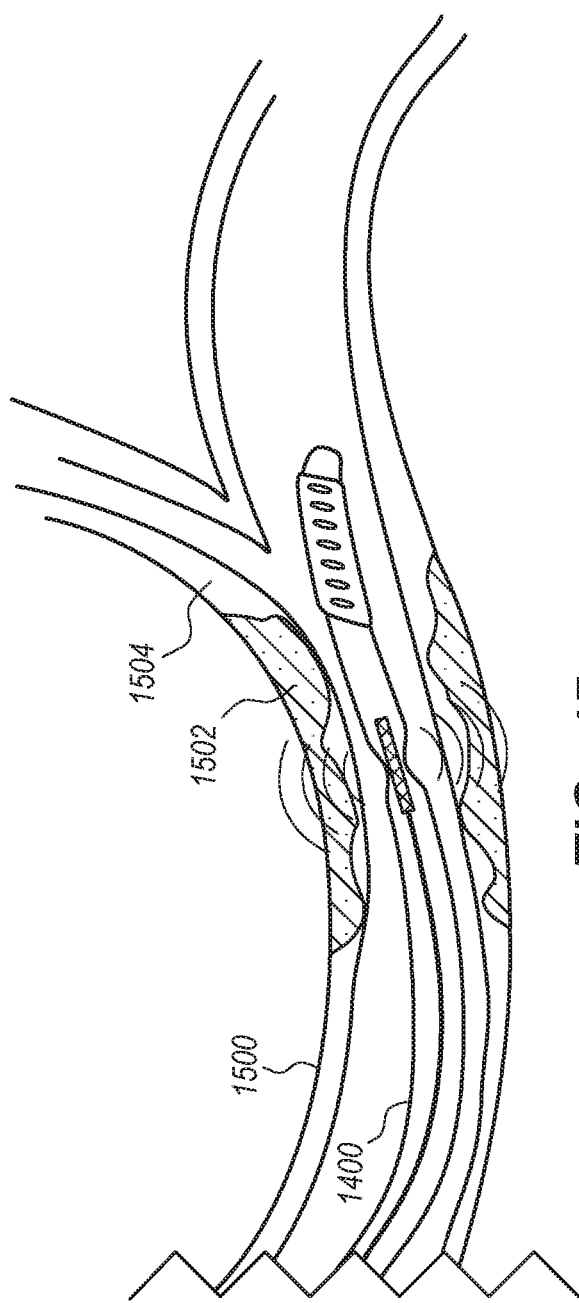
FIG. 15 is a schematic cross-sectional view of an embodiment of a portion of the photoacoustic catheter disposed within a vessel.

The light guides herein can be disposed inside the elongate shaft of a photoacoustic catheter. Referring now to FIGS. 14 and 15, schematic cross-sectional views of a photoacoustic catheter 1400 is shown in accordance with various embodiments herein. In FIG. 14, light guide 1402 is shown disposed inside of elongate shaft 1404 of photoacoustic catheter 1400. Light guide 1402 includes a photoacoustic transducer 1406 at the distal region of the light guide. Light within light guide 1402 is directed to photoacoustic transducer 1406, which converts light energy into an acoustic wave 1408 at the distal region of the light guide 1402. Acoustic wave 1408 is disposed radially about the light guide 1402. Acoustic waves may also be directed axially from the transducer if the transducer is located at the distal end of the light guide 1402. The photoacoustic catheter 1400 can include a flexible tip 1410 at the distal end. The flexible tip 1410 can be configured to assist with steering the photoacoustic catheter to a treatment location. In some application, the light guide does not include a flexible tip. The lack of a tip structure allows therapy to be directed forward axially in addition to radially. It is appreciated that light guide 1402 can include more than one photoacoustic transducer along its elongate shaft.

FIG. 15 shows photoacoustic catheter 1400 disposed within a vessel 1500. Vessel 1500 includes a vessel wall 1504 and a calcified lesion 1502 disposed within the vessel wall. In some embodiments, the calcified lesion can be found adjacent to the vessel wall.

Figure 16:
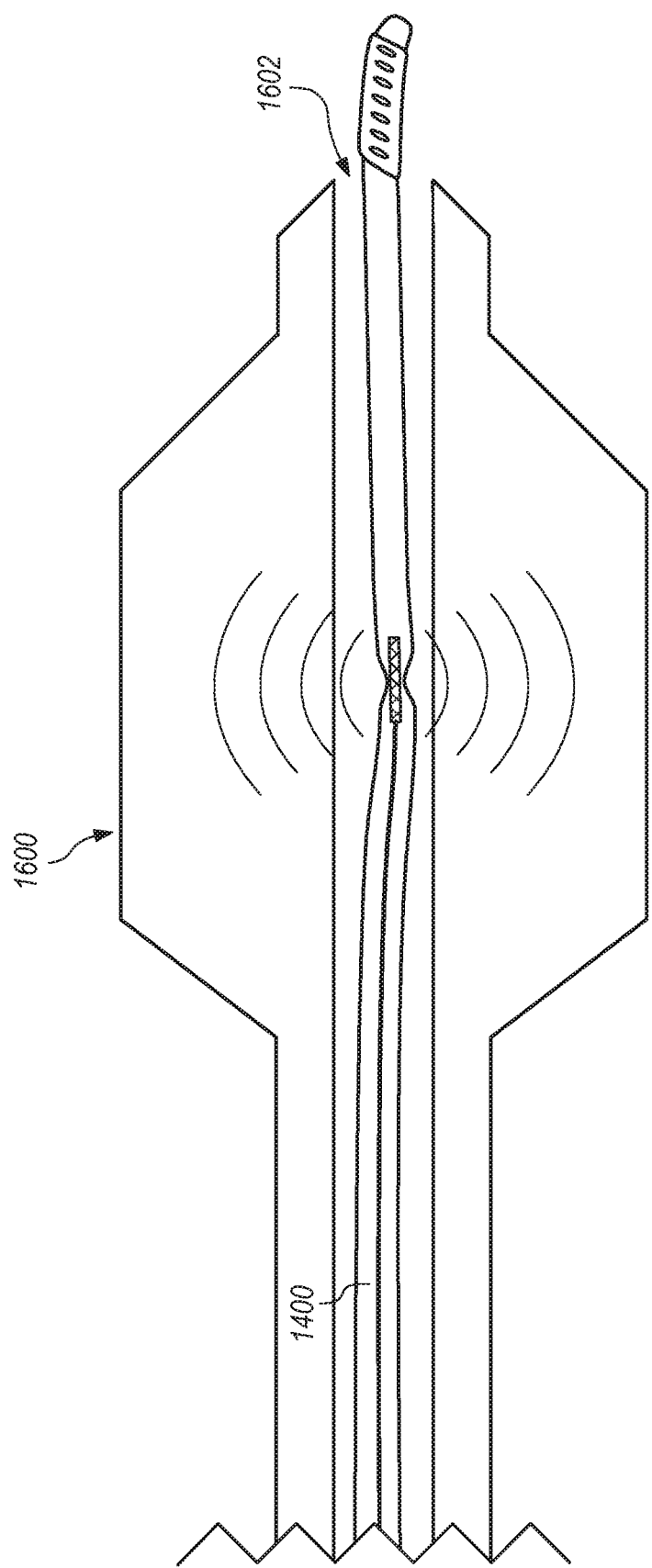
FIG. 16 is a schematic cross-sectional view of another embodiment of a portion of the photoacoustic catheter.

The photoacoustic catheter 1400 can be used as is, or it can also be used with many different types of inflatable balloons that have an accessible central lumen that can accommodate the photoacoustic catheter. Referring now to FIG. 16, a schematic cross-sectional view of a photoacoustic catheter 1400 placed within a balloon catheter 1600 having an inflatable balloon is shown in accordance with various embodiments herein. During a method for using acoustic pressure waves to induce fractures upon a calcified lesion within or adjacent a vessel wall, a practitioner can introduce an inflatable balloon to the site of a calcified lesion. It is possible for the photoacoustic catheter 1400 to be in place before the balloon catheter 1600 is advanced to the treatment site, such as if the photoacoustic catheter has a flexible tip configured to help steer to a treatment site. Alternatively, the balloon catheter 1600 may be located at the treatment site before the photoacoustic catheter 1400 is advanced along a central lumen 1602 to the treatment site. When the inflatable balloon has been placed at the site of the calcified lesion, the practitioner can then inflate the balloon. Inflation of the balloon may help with maintaining the location of the photoacoustic catheter 1400 at the treatment site, help with treatment of the vascular lesion by applying pressure to the vessel wall, or both.

Methods

A method for using acoustic pressure waves to induce fractures upon a calcified lesion within or adjacent a vessel wall is included herein. The method can include providing a photoacoustic catheter adapted for placement within a blood vessel having a vessel wall. The catheter can include a first light guide and a first photoacoustic transducer disposed within a distal region of the first light guide. The first photoacoustic transducer can be in optical communication with the first light guide and can be adapted to generate acoustic pressure waves. The first photoacoustic transducer can include a light-absorbing material and a thermal expansion material. The method can include activating a light source in optical communication with the first light guide, thereby imparting acoustic pressure waves upon a calcified lesion within or adjacent a vessel wall to induce fractures in the calcified lesion.

In some embodiments, the photoacoustic catheter used in the methods herein can include an inflatable balloon disposed about the photoacoustic transducer and coupled to the elongate shaft. The method can further include inflating the balloon from a collapsed configuration suitable for advancing the catheter through a patient's vasculature to an expanded configuration suitable for anchoring the catheter in position relative to a treatment site. The expanded configuration may also help with treatment of the vascular lesion by applying pressure to the vessel wall.

In various embodiments, the inflatable balloon is inflated with saline solution, contrast fluid visible using imaging equipment, or a mix of both.

Light Guides

The light guides herein can include an optical fiber or flexible light pipe. The light guides herein can be thin and flexible and can allow light signals to be sent with very little loss of strength. The light guides herein can include a core surrounded by a cladding about its circumference. In some embodiments, the core can be a cylindrical core or a partially cylindrical core. The core and cladding of the light guides can be formed from one or more materials, including but not limited to one or more types of glass, silica, or one or more polymers. The light guides may also include a protective coating, such as a polymer. It is appreciated that the index of refraction of the core will be greater than the index of refraction of the cladding.

Each light guide can guide light along its length to a distal end having a photoacoustic transducer connected thereto. The light guide can create a light path as portion of an optical network including a light source. The light path within the optical network allows light to travel from one part of the network to another without being modified. Both the optical fiber or the flexible light pipe can provide a light path within the optical networks herein.

There are a number of different options for the position of and configuration of one or more photoacoustic transducers. In one option, light may propagate out the end of the light guide where a photoacoustic transducer is integrated on the end of the light guide. In addition, or alternatively, the cladding of the light guide is modified so that some or all of the light is transmitted out the side of the light guide to energize the photoacoustic transducer that is integrated on the side of the light guide. In addition, or alternatively, the light propagates out the light guide and travels through free space or some other media to impinge on a photoacoustic transducer material after some propagation distance outside of the light guide.

To create photoacoustic transducers along the light guide, at least a portion of the cladding is removed or modified to provide an opening in the cladding that exposes a region of the light guide core for optical communication with the photoacoustic transducer. In some embodiments, the portion of the cladding that is removed can be in the shape of a square, a circle, and oval, a trapezoid, and the like. In some embodiments, the portion of the cladding removed from the light guide can extend circumferentially about the entire light guide. In other embodiments, the portion of the cladding removed from the light guide can extend circumferentially about a portion of the light guide. In yet other embodiments, the portion of the cladding removed from the light guide can be in the shape of a spiral circumferentially disposed about a portion of the light guide.

The light guides herein can come in various sizes and configurations. The light guides will have a longitudinal axis along the elongate shaft of the light guide and short axis about its circumference. In some embodiments, the light guides can have an outer diameter of about 100 um, including the cladding and the core. In other embodiments, the light guides can include those that have an outer diameter of from 50 um to 1000 um including the cladding and the core. The length of the light guides can include those having a length of from 40-175 cm. In some embodiments, the length of the light guides can include those having a length of from 50-150 cm. In some embodiments, the length of the light guide can include those having a length of 40 cm, 50 cm, 60 cm, 70 cm, 80 cm, 90 cm, 100 cm, 125 cm, 150 cm, or 175 cm. It is appreciated that the light guides herein can have a usable length that can fall within a range, wherein any of the forgoing lengths can serve as the lower or upper bound of the range, provided that the lower bound of the range is a value less than the upper bound of the range.

It is appreciated that one or more light guides herein can be adhered to the outside surface of the elongate shaft of a catheter, to create a photoacoustic catheter. However, in other embodiments, one or more light guides can be disposed within a lumen of a photoacoustic catheter. In addition, the photoacoustic catheter may define a lumen for a guidewire having an inner diameter of about 0.014 inch (0.356 mm). In some embodiments, the photoacoustic catheter can include those having an inner diameter of about 0.018 inch (0.457 mm). In yet other embodiments, the photoacoustic catheter can include those having an inner diameter of about 0.035 inch (0.889 mm). In some embodiments the light guides herein can be integrated with a balloon catheter. In some embodiments the light guides herein can be integrated into a guide wire. In embodiments where the light guide is integrated into a guide wire, the resulting photoacoustic catheter can be used independently or can be used with various other balloon catheters.

Photoacoustic Transducers

The photoacoustic transducers herein can include those that come in many shapes and sizes. As discussed elsewhere herein, the photoacoustic transducers disposed at the distal end of the light guides herein can assume the same shape as the distal end of the light guide, including but not limited to a conical shape, a convex shape, a concave shape, a bulbous shape, a square shape, a stepped shape, a half-circle shape, an ovoid shape, and the like. The photoacoustic transducers disposed along the longitudinal length of the light guides can include cylindrical transducers that are configured to span the entire circumference of light guide. In some embodiments a cylindrical transducer can be disposed at the distal end of a light guide. The photoacoustic transducers disposed along the length of the light guides can also include partial transducers that are configured to span at from at least 1 to 359 degrees about the light guide. In some embodiments, one photoacoustic transducer is disposed at the end of a light guide and one or more photoacoustic transducers are disposed along the length of the light guide.

The photoacoustic transducers herein can propagate pressure waves upon the site of a calcified lesion. The acoustic waves generated by the photoacoustic transducers can be tailored for the specific application, including directionality, shape, convergence, or divergence by tailoring the size, shape and excitation of the photoacoustic transducer(s). In some embodiments, the photoacoustic transducer(s) can be tailored to generate a cylindrical acoustic wave symmetrically about a light guide. In other embodiments, the photoacoustic transducers can be tailored to generate multiple acoustic waves from each light guide. In other embodiments, the photoacoustic transducers can be tailored to generate multiple acoustic waves that are directionally offset from one another by from zero degrees to 180 degrees about the elongate shaft of the light guide.

The length of each photoacoustic catheter can vary and can depend on the treatment location to be accessed. In some embodiments, the photoacoustic transducers can be from 0.1 mm to 6 mm, 0.1 mm to 2 mm, or 10 mm to 100 mm in length. In some embodiments, the photoacoustic transducers can be from 5 mm to 30 mm in length. In some embodiments, the photoacoustic transducers can be from 10 mm to 20 mm in length. A size for a single photoacoustic transducer of about 1 mm$^2$ or less is possible and has efficiency advantages over larger photoacoustic transducers. In other embodiments, the photoacoustic transducers can collectively span from 0.1 mm to 6 mm, 0.1 mm to 2 mm, 10 mm to 100 mm, from 5 mm to 30 mm along the elongate shaft of a photoacoustic catheter. In yet other embodiments, the photoacoustic transducers can exceed 30 mm in length, exceed 100 mm in length, such as in the context of coronary treatment, or exceed 200 mm in length, such as in the context of peripheral vascular treatment.

The photoacoustic transducers herein can include a light-absorbing material and a thermal expansion material. Exemplary light absorbing material suitable for use herein can include strong light-absorbing materials having large absorption coefficients of units inverse centimeters. Some exemplary light-absorbing materials can include, but not be limited to, nanoparticles, carbon nanotubes, candle soot, candle soot nanoparticles, carbon black, a nanotube array, multiwall carbon nanotubes, and light absorbing dyes. The light-absorbing materials herein can be highly absorbing of laser light such that absorption is rapid on the nanosecond timescale. The rapid absorption of light energy by the light-absorbing material can enable the efficient transfer of thermal energy to the thermal expansion material, thus driving the generation of acoustic waves.

Thermal expansion materials suitable for use herein can include materials having a strong coefficient of thermal expansion (CTE). For example, the thermal expansion material can have a coefficient of thermal expansion from 23 degrees Celsius to 100 degrees Celsius of about 0.000012 1/K or higher, about 0.0001 1/K or higher, 0.0002 1/K or higher, or about 0.0003 1/K or higher.

Suitable thermal expansion materials can include polymers having a strong coefficient of thermal expansion. Examples of suitable materials include, but are not to be limited to, polydimethylsiloxane (PDMS), polytetrafluoroethylene (PTFE), polyimide, polyisobutylene (PIB), PIB polyurethane, polyurethanes, styrene isoprene butadiene, ethylene propylene polyacrylic, ethylene acrylic, fluorosilicone, polybutadiene, polyisoprene, and thermoplastic elastomers. For a silicone PDMS material, the coefficient of thermal expansion from approximately 23 degrees Celsius to approximately 100 degrees Celsius can be about 0.00034 1/K. For a plain PTFE material, the coefficient of thermal expansion from 23 degrees Celsius to 100 degrees Celsius can be about 0.000143 1/K. For a polyimide material, the coefficient of thermal expansion from 23 degrees Celsius to 100 degrees Celsius can be about 0.00014 1/K.

Thermal expansion materials suitable for use herein can also include thin metallic films. Thin metallic films can be used alone, or in combination with additional thermal expansion materials, such as thermal expansion materials having a high coefficient of thermal expansion. Some exemplary metals for use as thermal expansion materials in thin metallic films include, but are not to be limited to silver, copper, and gold, aluminum, beryllium, tungsten, and magnesium.

The photoacoustic transducers herein can be formed by layering a light-absorbing material and a thermal expansion material on a surface of the light guides described herein. In some embodiments, the light-absorbing material and a thermal expansion material can form a composite film on or around the light guides described herein. In some embodiments, the composite film can include one that has layers of the light-absorbing material. In one embodiment, a layer of the light-absorbing material can be disposed on a light guide in optical contact with the core of the light guide and a thermal expansion material can be disposed on the surface of the light-absorbing material layer at the outermost surface. In some embodiments, the thermal expansion material is in thermal contact with the light absorbing material. In some embodiments, the thermal expansion material is in direct contact with the light absorbing material. In other embodiments, the thermal expansion material is in a matrix with the light absorbing material. In yet other embodiments, the thermal expansion material and the light absorbing material are the same.

One suitable configuration for the light-absorbing material and a thermal expansion material can include a layer of candle-soot nanoparticles as the light-absorbing material in contact with a layer of polydimethylsiloxane as the thermal expansion material. Another suitable configuration for the light-absorbing material and a thermal expansion material can include a layer of multiwall carbon nanotubes as the light-absorbing material in contact with a layer of polydimethylsiloxane as the thermal expansion material.

The light-absorbing material and a thermal expansion material can be applied to the light guides using various techniques. In some embodiments, the light-absorbing material and a thermal expansion material can be individually applied to the light guides using a spray coating technique. In other embodiments, the light-absorbing material and a thermal expansion material can be individually applied to the light guides using a dip coating technique.

Acoustic Waves

The photoacoustic catheters herein can generate acoustic waves having pressures in the range of 2 megapascals (MPa) to 25 MPa. The maximum pressure of a particular photoacoustic catheter will depend on the light source, the absorbing material, the propagation medium, and other facture. In some embodiments, the photoacoustic catheters herein can generate acoustic waves having peak or maximum pressures in the range of 5 MPa to 20 MPa. In some embodiments, the photoacoustic catheters herein can generate acoustic waves having peak pressures of about 1 MPa, 2 MPa, 3 MPa, 4 MPa, 5 MPa, 6 MPa, 7 MPa, 8 MPa, 9 MPa, 10 MPa, 11 MPa, 12 MPa, 13 MPa, 14 MPa, 15 MPa, 16 MPa, 17 MPa, 18 MPa, 19 MPa, 20 MPa, 21 MPa, 22 MPa, 23 MPa, 24 MPa, or 25 MPa. It is appreciated that photoacoustic catheters herein can generate acoustic waves having operating pressures or peak pressures that can fall within a range, wherein any of the forgoing numbers can serve as the lower or upper bound of the range, provided that the lower bound of the range is a value less than the upper bound of the range.

Therapeutic treatment can act via a fatigue mechanism or a brute force mechanism. For a fatigue mechanism, operating pressures would be about 0.5 MPa to 2 MPa, or about 1 MPa. For a brute force mechanism, operating pressures would be about 20 MPa to 30 MPa, or about 25 MPa. Pressures between the extreme ends of these two ranges may act upon a calcified lesion using a combination of a fatigue mechanism and a brute force mechanism.

Fiber Diffusers

A fiber diffuser directs light from within a light guide to exit at a side surface of the light guide. The fiber diffusers described herein can be created several ways. In some embodiments, the fiber diffusers can be created by micromachining the surface of the distal end of a light guide with a $CO_2$ laser. In some embodiments, a fused silica coating can be applied to the distal end of the light guide. In other embodiments, the fiber diffuser can be formed from a glass, a polymer, or a metal coating on the distal end of the light guide. In other embodiments, the fiber diffuser can be formed by a fiber Bragg grating on the distal end of the light guide. In some embodiments, the fiber diffuser can include a machined portion of the light guide, a laser-machined portion of the light guide, fiber Bragg gratings, a fused splicing, a fused splicing forming at least one internal mirror, and a splicing of two or more diffuse regions. Suitable materials for a fiber diffuser can include, but not be limited to, the materials of the core or cladding, ground glass, silver coated glass, gold coated glass, $TiO_2$, and other materials that will scatter and not significantly absorbed the light wavelength of interest. One method that can be used to create a uniform diffuser in a light guide, optical component, or materials is to utilized scattering centers on the order of 50 nanometers to 5 micrometers in size. The scattering centers can have a distribution around 200 nanometers in size.

Light Sources

The light sources suitable for use herein can include various types of light sources including lasers and lamps. Suitable lasers can include short pulse lasers on the nanosecond (ns) timescale. The lasers can also include short pulse lasers on the picosecond (ps), femtosecond (fs), and microsecond (us) timescales.

Exemplary nanosecond lasers can include those within the UV to IR spectrum, spanning wavelengths of about 10 nanometers to 1 millimeter. Nanosecond lasers can include those having repetition rates of up to 200 kHz. In some embodiments, the laser can include a Q-switched Tm:YAG laser. In some embodiments, the laser can include an Nd:YAG, Ho:YAG, Er:YAG, excimer laser, Helium-Neon laser, Carbon Dioxide laser, as well as doped, pulsed, fiber lasers.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

As used herein, the recitation of numerical ranges by endpoints shall include all numbers subsumed within that range, inclusive (e.g., 2 to 8 includes 2, 2.1, 2.8, 5.3, 7, 8, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it is understood that many variations and modifications may be made while remaining within the spirit and scope herein.

It is understood that although a number of different embodiments of the photoacoustic catheter have been illustrated and described herein, one or more features of any one embodiment can be combined with one or more features of one or more of the other embodiments, provided that such combination satisfies the intent of the present invention.

While a number of exemplary aspects and embodiments of the photoacoustic catheter have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A photoacoustic catheter for placement within a blood vessel having a vessel wall, the photoacoustic catheter for treating a calcified lesion within or adjacent to the vessel wall, the photoacoustic catheter comprising:
    an elongate shaft extending from a proximal region to a distal region, the elongate shaft including a first light guide, the first light guide being in optical communication with a light source; and
    a first photoacoustic transducer disposed within the distal region of the elongate shaft, the first photoacoustic transducer being in optical communication with the first light guide, the first photoacoustic transducer adapted to impart acoustic pressure waves upon the calcified lesion to induce fractures in the calcified lesion, the first photoacoustic transducer including a layer of light-absorbing material and a separate layer of thermal expansion material, the layer of light-absorbing material and the layer of thermal expansion material being individually applied to the light guide.

2. The photoacoustic catheter of claim 1 wherein the layer of thermal expansion material is in thermal contact with the layer of light absorbing material, and wherein the thermal expansion material is selected from a group consisting of polydimethylsiloxane, polytetrafluoroethylene, polyimide, polyisobutylene, polyisobutylene polyurethane, polyurethanes, styrene isoprene butadiene, ethylene propylene polyacrylic, ethylene acrylic, fluorosilicone, polybutadiene, polyisoprene, and thermoplastic elastomers.

3. The photoacoustic catheter of claim 1 wherein the light-absorbing material is selected from the group consisting of nanoparticles, carbon nanotubes, candle soot, candle soot nanoparticles, carbon black, a nanotube array, multiwall carbon nanotubes, and light absorbing dye.

4. The photoacoustic catheter of claim 1 wherein the first light guide is an optical fiber and the light source is a laser.

5. The photoacoustic catheter of claim 1 further comprising:
    a second light guide within the elongate shaft, wherein the second light guide is in optical communication with the light source; and
    a second photoacoustic transducer disposed within the distal region of the elongate shaft, the second photoacoustic transducer being in optical communication with the second light guide, the second photoacoustic transducer adapted to impart acoustic pressure waves upon the calcified lesion to induce fractures in the calcified lesion, the second photoacoustic transducer including a layer of light-absorbing material and a separate layer of thermal expansion material.

6. The photoacoustic catheter of claim 1 wherein the distal end of the first light guide has a shape selected from the group consisting of a cylindrical end, an angled end, a tapered end, and a conical end.

7. The photoacoustic catheter of claim 1 wherein the distal end of the first light guide has a side surface and a diverter, the diverter directing light in the first light guide toward the side surface, the diverter including one of a reflecting element and a refracting element.

8. The photoacoustic catheter of claim 1 wherein the distal end of the first light guide has a side surface, and the first photoacoustic transducer is positioned on the side surface of the first light guide.

9. The photoacoustic catheter of claim 1 wherein the first light guide includes a side surface and a fiber diffuser, the first fiber diffuser directing light from the first light guide to exit the first light guide at the side surface, the side surface being in optical communication with the first photoacoustic transducer.

10. The photoacoustic catheter of claim 9 further comprising a second photoacoustic transducer and a second fiber diffuser, each fiber diffuser directing light from the first light guide to exit the first light guide at the side surface, the side surface being in optical communication with each of the photoacoustic transducers.

11. The photoacoustic catheter of claim 10 wherein the first light guide includes a non-emitting portion, the photoacoustic transducers being axially spaced apart from one another with the non-emitting portion being disposed between the photoacoustic transducers.

12. The photoacoustic catheter of claim 9 wherein the first fiber diffuser is selected from the group consisting of a machined portion of the first light guide, a laser-machined portion of the first light guide, fiber Bragg gratings, a fused splicing forming at least one internal mirror, and a splicing of two or more diffuse regions.

13. The photoacoustic catheter of claim 1 wherein the layer of light-absorbing material is disposed on optical contact with the light guide, and the layer of thermal expansion material is disposed onto a surface of the light-absorbing material.

14. The photoacoustic catheter of claim 1 wherein the layer of the light-absorbing material is disposed on the light guide in optical contact with a core of the light guide and the layer of thermal expansion material is be disposed on an outermost surface of the layer of light-absorbing material.

15. A method comprising the step of:
    inducing fractures upon a calcified lesion that is within or adjacent to a vessel wall by generating acoustic pressure waves with a photoacoustic catheter that includes (i) a light guide and (ii) a photoacoustic transducer disposed within a distal region of the light guide and in optical communication with the light guide, the photoacoustic transducer including a layer of light-absorbing material and a separate layer of thermal expansion material, the layer of light-absorbing material and the layer of thermal expansion material being individually applied to the light guide.

16. The method of claim 15 wherein the layer of thermal expansion material is in thermal contact with the layer of light absorbing material, and wherein the thermal expansion material is selected from a group consisting of polydimethylsiloxane, polytetrafluoroethylene, polyimide, polyisobutylene, polyisobutylene polyurethane, polyurethanes, styrene isoprene butadiene, ethylene propylene polyacrylic, ethylene acrylic, fluorosilicone, polybutadiene, polyisoprene, and thermoplastic elastomers.

17. The method of claim 15 wherein the light-absorbing material is selected from the group consisting of nanoparticles, carbon nanotubes, candle soot, candle soot nanoparticles, carbon black, a nanotube array, multiwall carbon nanotubes, and light absorbing dye.

18. The method of claim 15 further comprising the step of diverting light in the light guide toward a side surface of the light guide with a diverter that includes one of a reflecting element and a refracting element.

19. The method of claim 15 further comprising the step of directing light from the light guide to exit the light guide at a side surface of the light guide with a fiber diffuser, the side surface being in optical communication with the photoacoustic transducer.

20. A photoacoustic catheter for treating a calcified lesion, the photoacoustic catheter comprising:
- an elongate shaft extending from a proximal region to a distal region, the elongate shaft including a light guide that includes an optical fiber, the light guide being in optical communication with a light source that includes a laser, the light guide including a side surface and a diverter, the diverter directing light in the light guide toward the side surface, the diverter including one of a reflecting element and a refracting element; and
- a photoacoustic transducer disposed within the distal region of the elongate shaft, the photoacoustic transducer being in optical communication with the light guide, the photoacoustic transducer being adapted to selectively impart acoustic pressure waves upon the calcified lesion to induce fractures in the calcified lesion, the photoacoustic transducer including a layer of light-absorbing material and a separate layer of thermal expansion material, the layers of material being individually applied to the light guide;
- wherein the light-absorbing material is selected from the group consisting of nanoparticles, carbon nanotubes, candle soot, candle soot nanoparticles, carbon black, a nanotube array, multiwall carbon nanotubes, and light absorbing dye;
- wherein the thermal expansion material is selected from the group consisting of polydimethylsiloxane (PDMS), polytetrafluoroethylene (PTFE), polyimide, polyisobutylene (PIB), PIB polyurethane, polyurethanes, styrene isoprene butadiene, ethylene propylene polyacrylic, ethylene acrylic, fluorosilicone, polybutadiene, polyisoprene, and thermoplastic elastomers;
- wherein the layer of light-absorbing material and the layer of thermal expansion material form a composite film around the light guide.

* * * * *